United States Patent [19]
Baumgartner et al.

[11] Patent Number: 5,206,602
[45] Date of Patent: Apr. 27, 1993

[54] BIOMEDICAL AMPLIFIER CIRCUIT

[75] Inventors: Richard A. Baumgartner, Palo Alto, Calif.; Charles E. Moore, Loveland, Colo.

[73] Assignee: Hewlett-Packard Company, Palo Alto, Calif.

[21] Appl. No.: 876,612

[22] Filed: Apr. 30, 1992

[51] Int. Cl.⁵ .............................................. M03F 1/02
[52] U.S. Cl. .......................................... 330/9; 330/258
[58] Field of Search ................... 330/9, 252, 253, 257, 330/258, 260, 277

[56] References Cited

U.S. PATENT DOCUMENTS

| | | | |
|---|---|---|---|
| 4,912,423 | 3/1990 | Milkovic et al. | 330/9 |
| 4,933,644 | 6/1990 | Fattaruso et al. | 330/258 |
| 4,947,135 | 8/1990 | Mijuskovic | 330/9 |

Primary Examiner—Steven Mottola

[57] ABSTRACT

A mixed analog and digital integrated circuit with features which are especially useful for application as a front end for physiological signal instrumentation such as electrocardiographs, electromyographs, and electroencephalographs. The integrated circuit has 5 signal channels, each with analog amplification and analog to digital conversion. The channels can be configured for various combinations of input signal amplification, input signal summation, analog output driving, and AC impedance measurement. The integrated circuit has 2 digital serial input lines and 2 digital serial output lines, all designed for direct connection to optical couplers. Channel configuration, gain, and other parameters are externally controllable by a serial digital input signal. Up to 6 compatible devices can be serially connected in a chain.

6 Claims, 24 Drawing Sheets

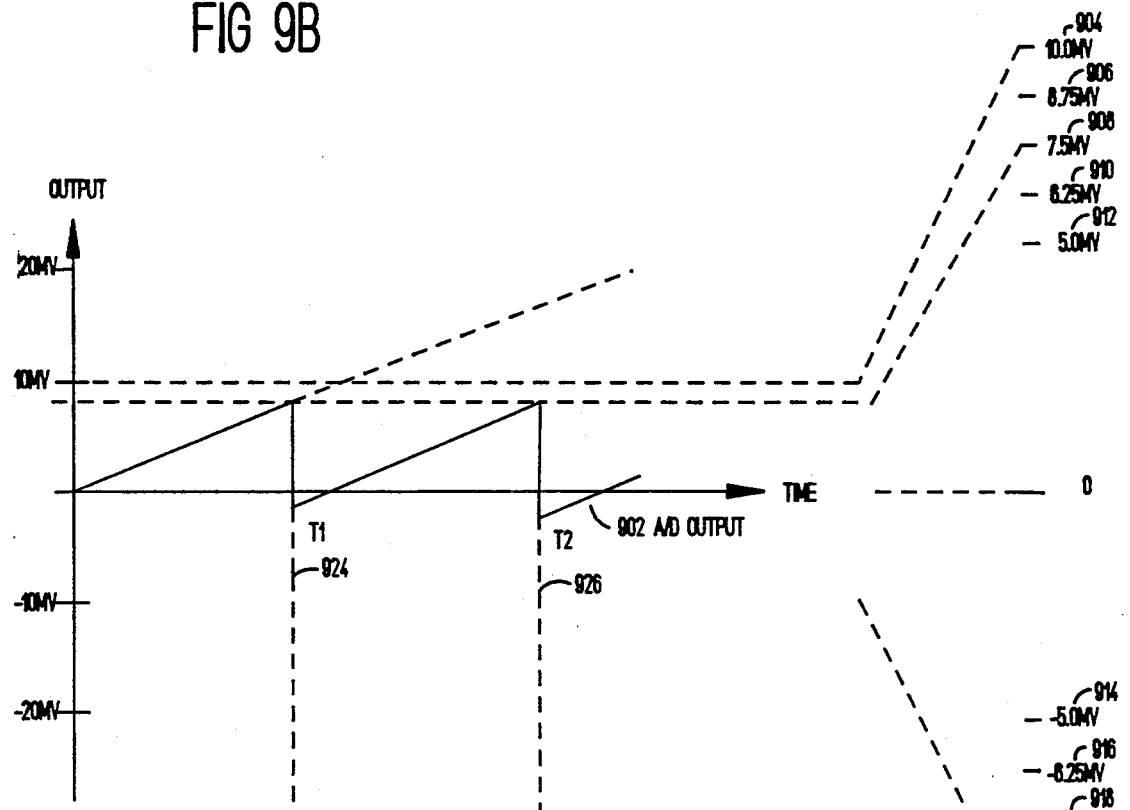
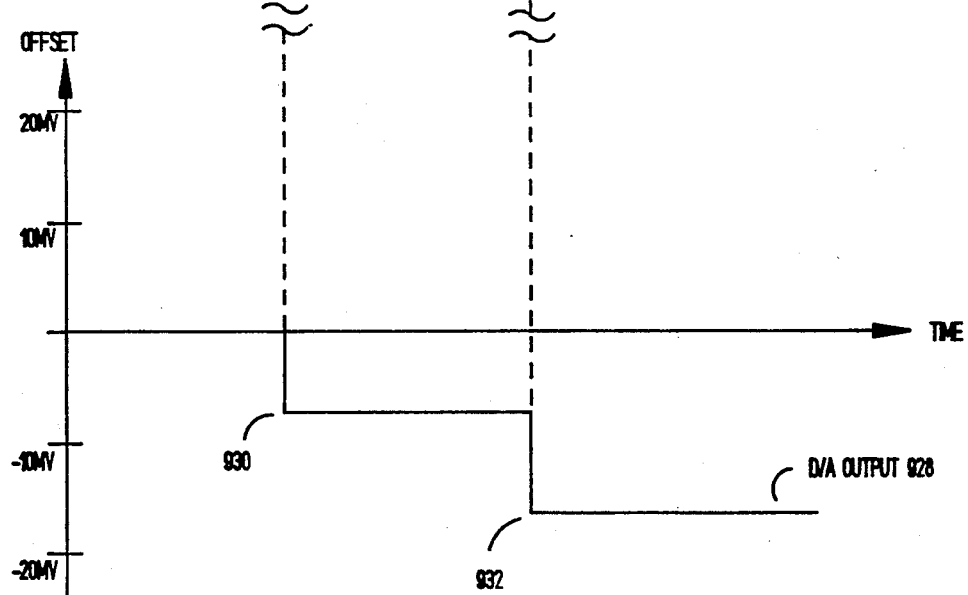

BIOMEDICAL AMPLIFIER CIRCUIT

CROSS REFERENCE TO RELATED APPLICATIONS

U.S. Ser. No. 07/876,645, filed Apr. 30, 1992, Integrated Circuit for Physiological Measurement, by Richard Albert Baumgartner, Charles Everett Moore, and Earl Clark Herleikson.

U.S. Ser. No. 07/876,611, filed Apr. 30, 1992, Analog to Digital Converter with Autoranging Offset, by Richard Albert Baumgartner, Charles Everett Moore, and Earl Clark Herleikson.

U.S. Ser. No. 07/876,841, filed Apr. 30, 1992, Signal Processing Circuits with Digital Programmability, by Richard Albert Baumgartner and Earl Clark Herleikson.

U.S. Ser. No. 07/876,546, filed Apr. 30, 1992, Signal Processing Circuits with Serial Chaining, by Richard Albert Baumgartner, Charles Everett Moore, and Earl Clark Herleikson.

FIELD OF INVENTION

This invention relates generally to biomedical instrumentation and more particularly to a mixed analog and digital integrated circuit for the front end of physiological signal instrumentation such as electrocardiographs, electromyographs, and electroencephalographs.

BACKGROUND OF THE INVENTION

Many useful medical signal instruments require processing of voltages resulting from muscle or nerve activity within a living being. For example, an electrocardiograph (ECG) measures voltages on the surface of the body that originate from nerve and muscle activity involved in the pumping action of heart muscles. Similarly, electromyographs measure voltages on the surface of the body that originate from muscle activity. Electroencephalographs measure voltages on the surface of the skull that result from aggregate chemical and neuron activity in the brain. Physiological signal measurements typically require surface electrodes, usually small conductive discs or pads attached to the skin with a conductive gel.

In addition to voltage measurements, some physiological information of interest may be detected by measurement of impedance. For example, the resistance of the chest varies with the volume of contained air. Therefore, chest impedance can be used to measure respiration. Another use of impedance measurement is to detect whether electrodes are adequately attached.

A front end for a signal measurement instrument is the circuitry directly interfacing to the signal of interest. Front ends for physiological signal measurements require high input impedance, low noise, high gain amplifiers. Contact resistance between an electrode and the body surface can be as high as 1 Megohm. Signal levels can vary from a few microvolts for electroencephalographic activity to a few millivolts for muscle activity.

Usually, in physiological signal measurement, the signals of interest are several orders of magnitude smaller than electrical noise levels. Metal electrodes in contact with conductive gels and natural body electrolytes create battery-like electrochemical processes which can produce DC offset voltages on the order of 100 mV. This offset may change with movement, for example respiration. Amplifiers also typically have some DC offset voltage at the input as well as some very low frequency noise (1/f noise). 50 Hz or 60 Hz power lines can produce voltages on the order of 20 V p-p on the surface of the body. Fluorescent lights can create 100 Hz or 120 Hz bursts of higher frequency noise. Other sources of noise include cardiac pacemakers and electronic scalpels. Therefore, extracting a signal from noise is a requirement for physiological signal instrumentation.

Of particular interest in an ECG application is measurement of late potentials. These are very low level voltages following the R-wave. Low noise is essential to discriminate subtle changes in these low level signals.

Typically, the signals of biomedical interest are relatively low frequency. For example, the frequencies of interest in ECG's are less than 500 Hz. Therefore, low pass filters may be used to remove some noise. In addition, analog offset subtraction or high-pass filtering is needed to remove DC offset voltages.

Some noise such as 50 Hz or 60 Hz power line noise is mostly common mode noise (same magnitude over the entire body surface). Physiological signals are typically measured differentially (voltage of one electrode relative to another electrode) so that common mode noise voltages can be eliminated by using differential amplifiers with high common mode rejection. An alternative way to reduce common mode signals is to subtract the common mode signal at the patient. This may be accomplished by measuring the common mode (summation of signals) and driving the patient with an opposite polarity voltage. For example, see Bruce B. Winter and John G. Webster, *Driven-Right-Leg Circuit Design*, IEEE Transactions on Biomedical Engineering, Vol. BME-30, No. 1, January 1983, pp 62-65.

Another requirement for physiological instrumentation is safety; protection of the patient from electrical shock. Any circuitry directly connected to a patient must be battery powered or isolated from normal AC power sources. In addition, the currents in any signals used for common mode offset or impedance measurement must be limited. For example, see *American National Standard for Diagnostic Electrocardiographic Devices*, ANSI/AAMI EC11-1982 (available from the Association for the Advancement of Medical Instrumentation).

In addition to protection of the patient, there are also requirements for protection of the instrumentation input circuitry. For example, if the heart stops beating, a common procedure is to apply a large voltage pulse (on the order of 5 KV) to synchronize the heart muscles (defibrillation). An ECG front end may be connected to the patient during defibrillation. In an emergency, where there is no time to attach normal ECG electrodes, the defibrillator paddles may also be connected directly to an ECG front end as ECG signal electrodes to provide a "quick look" at the electrocardiogram before defibrillation. The input circuitry of an ECG front end must be able to withstand defibrillator voltage pulses.

In addition to analog filtering and amplification, typical physiological signal instrumentation will include analog to digital conversion for further processing by an internal microprocessor or an external computer. Some multi-channel analog to digital conversion designs use a sample and hold circuit on each channel and a single high speed analog to digital circuit. Sample and hold circuits sample noise as well as signals. In addition, there may be time offsets between samples from different channels which can create spurious noise when measuring the digital difference between two channels. Continuous analog to digital conversion is useful to provide additional noise averaging and to avoid sample offset problems.

Analog to digital conversion circuits may have offset circuitry to extend the dynamic range. Monitoring an ECG in the presence of pacemakers or defibrillation presents special problems. Any offset circuit must be flexible or "intelligent" enough to ignore a single defibrillation pulse or periodic signals such as pacemaker pulses.

A typical modern instrument will also have digital control of various functions. Therefore, physiological signal instrumentation also requires a high frequency clocking signal and various digital circuitry. Digital clocking signals and circuitry create noise which may interfere with nearby analog circuitry. Therefore, additional noise reduction may be required to suppress digital noise. Common-mode noise suppression is especially important.

There is a need in the biomedical instrumentation field for large-scale integrated circuits having all the functionality described above: analog amplification with low noise and high input impedance, input protection, low pass filtering, DC offset subtraction, external common mode subtraction, internal common mode noise reduction, analog to digital conversion, impedance measurement, safety features (isolation from AC power and current limitation), plus additional calibration, configuration flexibility and convenience features.

SUMMARY OF THE INVENTION

The present invention is a mixed analog and digital integrated circuit (hereinafter, the Chip) with features which are especially useful for application as a front end for physiological signal instrumentation such as electrocardiographs, electromyographs, and electroencephalographs.

The Chip incorporates novel circuit designs to implement precision analog performance in a mixed analog and digital IC. The analog preamps are a novel design having differential chopper stabilized common mode feedback within a differential chopper stabilized signal amplifier. Very high open loop gain is achieved by the use of multiple cascode stages. Additional common mode rejection is achieved by cross-coupled current mirrors in the amplifier load circuitry. The resulting amplifiers have high input impedance, low noise levels at low frequencies, and high common mode rejection.

BRIEF DESCRIPTION OF THE DRAWINGS

FIG. 9B illustrates the output of the A/D converter in response to the sample waveform illustrated in FIG. 9A.

FIG. 9C illustrates the output of the autoranging offset circuit in response to the sample waveform illustrated in FIG. 9A.

DETAILED DESCRIPTION OF THE PREFERRED EMBODIMENT OF THE INVENTION

TABLE OF CONTENTS

I. Overview
II. Analog Input Amplifiers
III. Analog to Digital Conversion
IV. Switched Capacitor Circuits
V. Analog Averaging
VI. Input Switching and Leads-Off Detection
VII. Impedance measurement
VIII. Serial Chaining of Multiple Chips
IX. Digital Control

I. OVERVIEW

Figure 1:
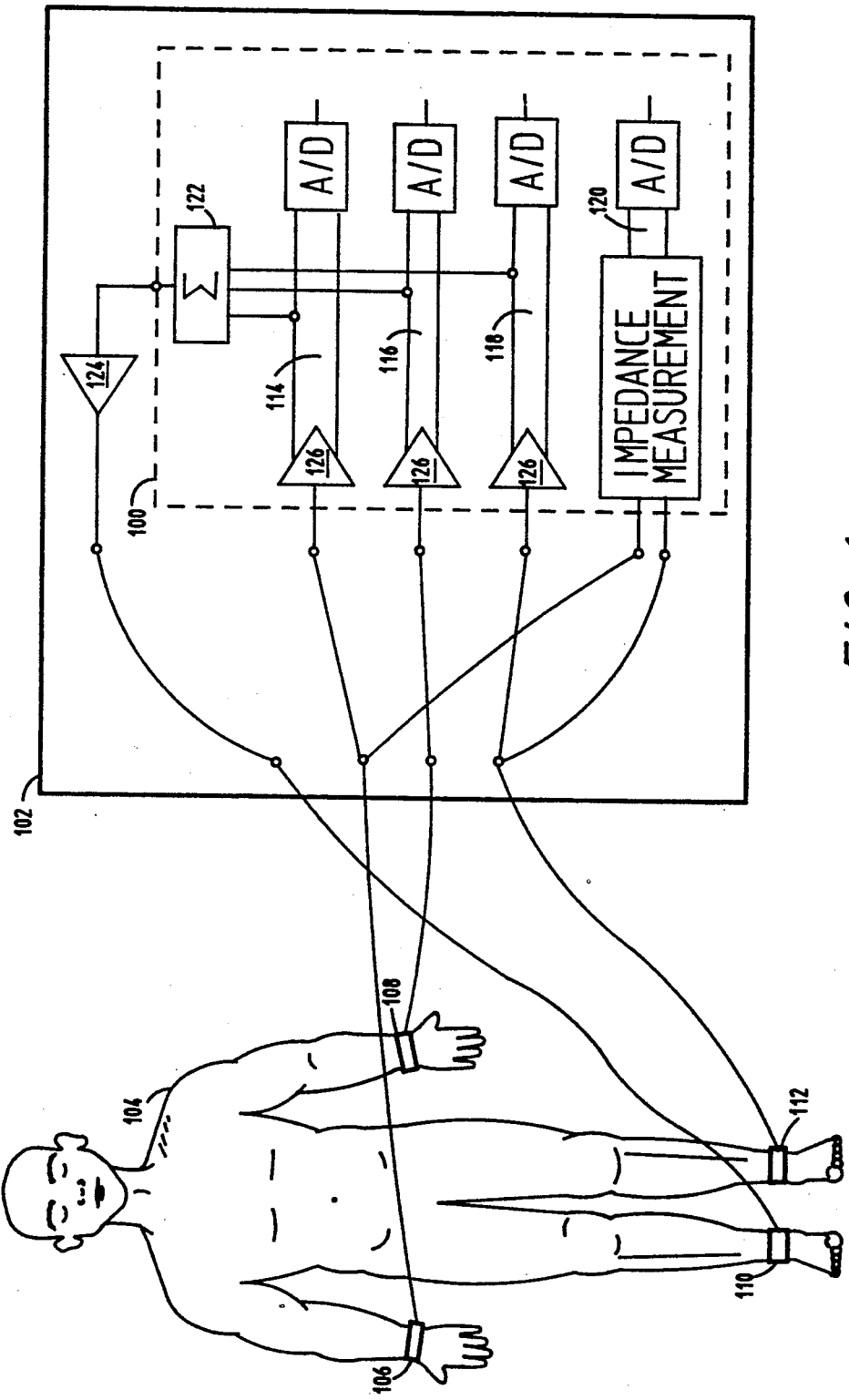
FIG. 1 is a schematic representation of a patient connected to an electrocardiograph system which includes the present invention.

FIG. 1 depicts a patient 104 connected to a electrocardiograph 102. Four electrodes are connected to the patient; one on each arm (106, 108), and one on each leg (110, 112). A common arrangement for an electrocardiograph is to monitor three differential voltages, left arm 108 to right arm 106, left leg 112 to right arm 106, and left leg 112 to left arm 108. However, other combinations may be selected as needed.

As depicted in FIG. 1, the functional blocks depicted within the dashed area 100 represent one possible configuration of the present invention. As depicted in FIG. 1, 3 channels (114, 116, and 118) are configured as signal amplifiers. In addition, the right arm lead 106 and the left leg lead 112 are also being used by a fourth channel 120 to monitor respiration. Channels 114, 116 and 118 are added by summing circuitry 122 to create a patient common mode voltage. The common mode voltage output of the averaging circuitry 122 drives an external inverting amplifier 124 which in turn drives the right leg electrode 110 to subtract common mode noise, especially 50 Hz or 60 Hz power line noise, at the patient.

In FIG. 1, note that the three signal amplifiers (126) are single signal input, differential output amplifiers. Individual lead signals are amplified and digitized. Lead signal differences, such as right arm (106) to left arm (108) as described above, are implemented digitally within the instrument (102) and not within the Chip (100). The differential channels (114, 116, and 118) are useful for suppression of common mode noise internal to the Chip such as power supply noise and noise from adjacent digital circuitry.

Figure 2:
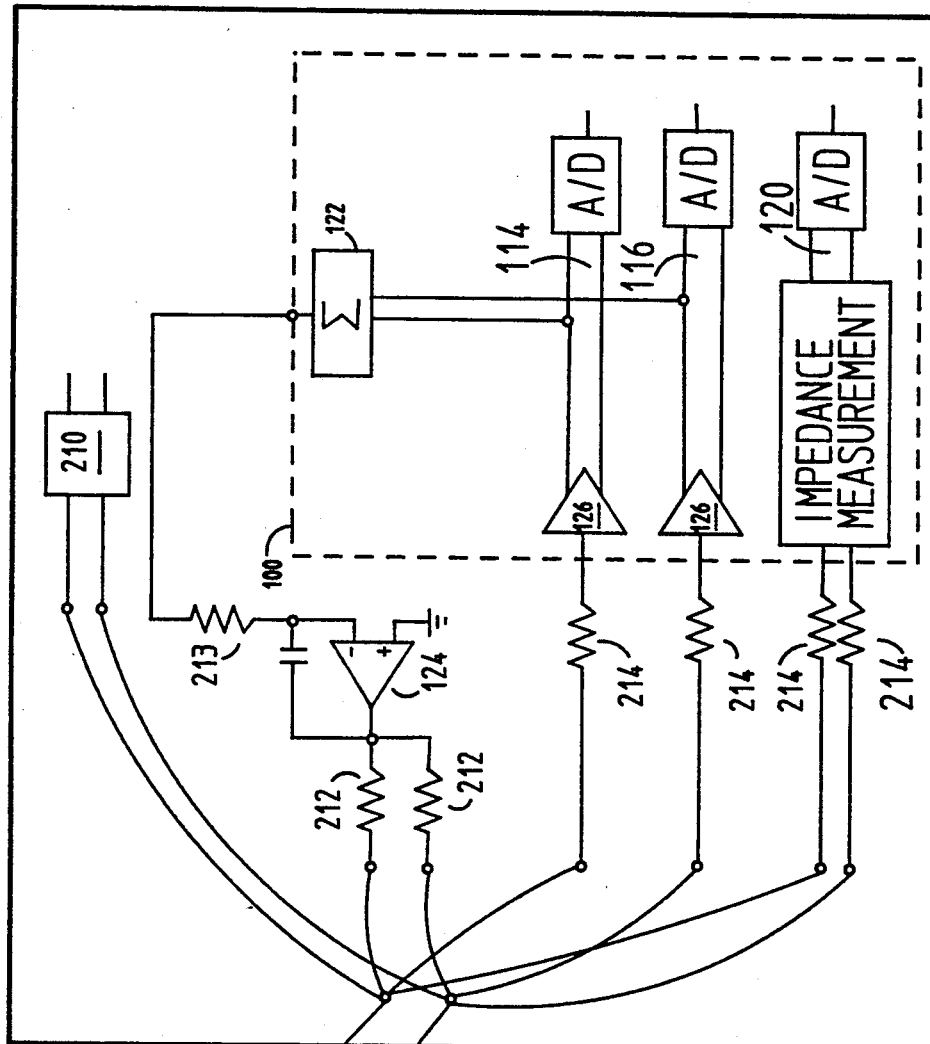
FIG. 2 is a schematic representation of a patient connected to a defibrillator system which includes the present invention.
Figure 2:
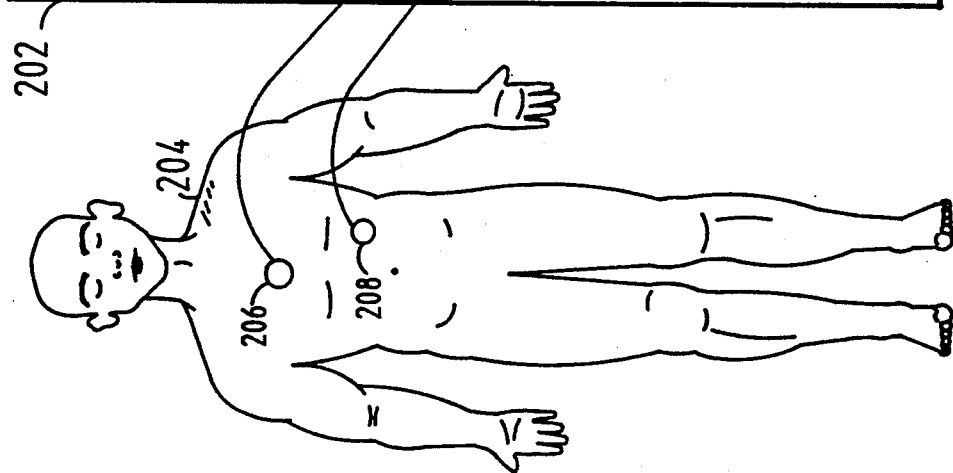

FIG. 2 depicts an alternative configuration for the present invention. In FIG. 2, a patient 204 is undergoing defibrillation. Box 202 depicts a defibrillator with circuit 210 representing a high voltage pulse capacitive discharge circuit which drives two defibrillator electrodes (206 and 208). The dashed box 100 represents a configuration of the present invention. In this configuration, two channels (114 and 116) of the Chip 100 are connected to the defibrillation paddles (206 and 208) as signal amplifiers for a "quick look" ECG before the defibrillation pulse is applied. External resistors 214 protect the signal amplifiers 126 from the high voltage defibrillation pulse. In addition, the averaging circuitry 122 (along with external amplifier 124 and external resistors 212 and 213) is used to drive both defibrillation paddles (206 and 208) to reduce common mode noise at the patient.

In FIG. 2, the internal AC impedance measurement circuitry 120 is used to detect whether there is adequate contact between the defibrillation paddles (206 and 208) and the patient 204. The same internal impedance circuitry is illustrated in FIG. 1 (120), with different frequency and current parameters, being used for respiration monitoring.

The configurations depicted in FIGS. 1 and 2 are only two of many configurations permitted by the present invention. As disclosed below, the Chip has five channels which can be configured via digital control signals to digitize up to five input voltage signals. Any combination of the five input signals can be summed to drive a sixth external lead (as illustrated in FIGS. 1 and 2) for common mode reduction at the patient. Alternatively, the invention can be configured via digital control signals to digitize input signals from any four of the five input leads and use any additive combination of the four input signals to drive the fifth lead as an output signal. Alternatively, one digitizing channel can be used for impedance measurement, which in turn is useful for monitoring respiration as depicted in FIG. 1 (120) or for detecting defibrillator electrode contact impedance as depicted in FIG. 2 (120). In some ECG diagnostic situations, 10 to 13 leads may be attached to the patient. As disclosed below, the present invention permits serial chaining of up to six Chips to provide up to 30 channels.

Figure 3:
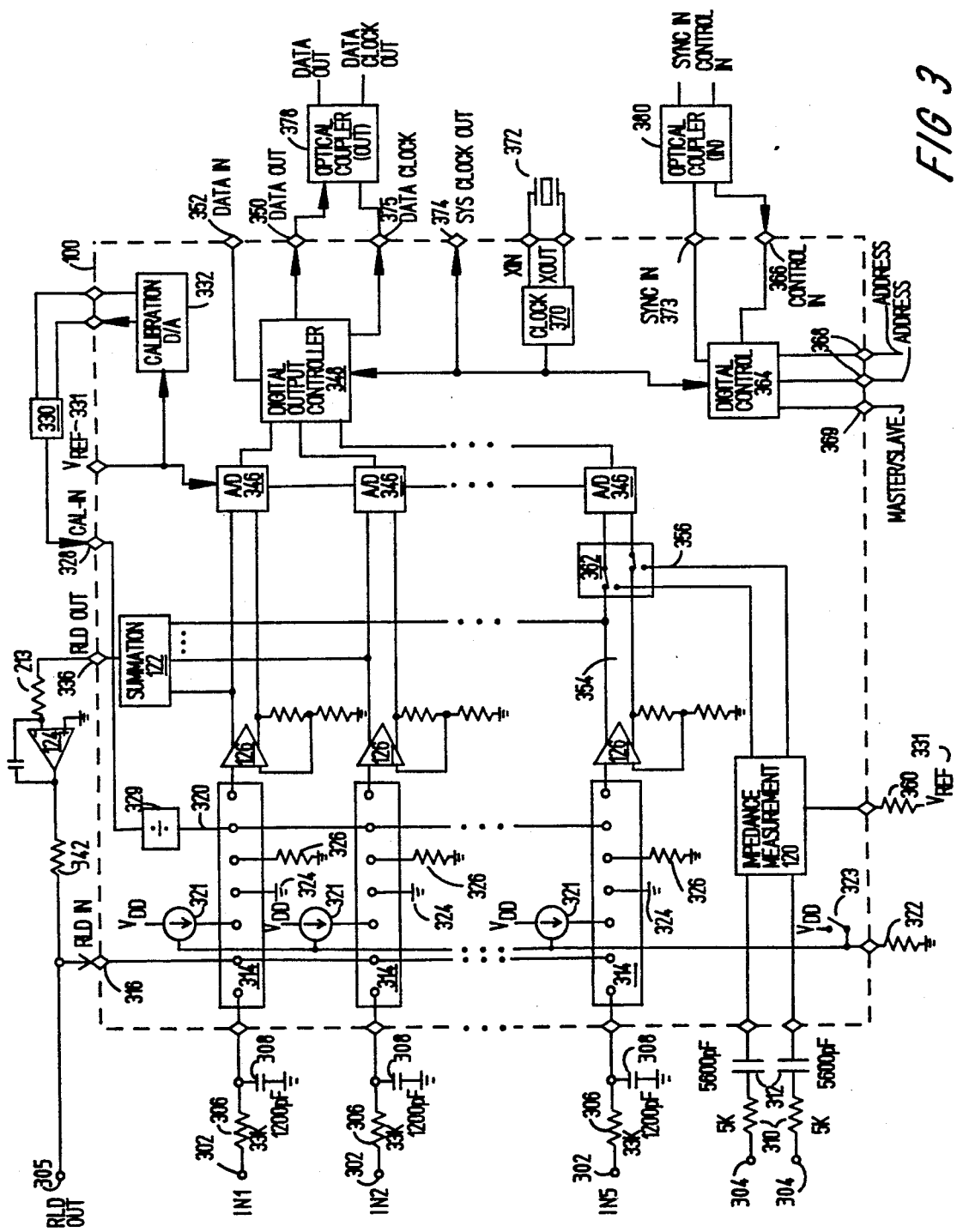
FIG. 3 is a schematic block diagram of the present invention along with some associated external circuitry.

FIG. 3 is a schematic block diagram of the Chip 100 and some associated external components and connections. The Chip 100 is the circuitry within the dashed line box. FIG. 3 illustrates 3 of 5 channels. In the preferred embodiment of the present invention, the Chip is used in a defibrillator/ECG application as illustrated in FIG. 2. Specific values of external components are disclosed for the defibrillator/ECG application. Other applications may require different external component values.

As illustrated in FIG. 3, there are five external switchable lead connections 302 (IN3 and IN4 are not shown), each of which is potentially an analog input voltage signal, an analog input voltage signal combined with a current source output for leads-off detection, or an output voltage signal for common mode compensation. In addition, there are two dedicated impedance measurement external lead connections 304 and a dedicated right-leg-drive (RLD) external connection 305.

Each switchable lead connection 302 is filtered by an external low pass RC filter comprising a series 33 Kohm resistor 306 and a 1,200 picofarad capacitor 308 to analog ground. Each impedance measurement lead connection 304 has an external 5 Kohm series resistor 310 and an external 5,600 picofarad series capacitor 312.

Each switchable lead connection 302 connects through an external series resistor 306 to an internal switching circuit 314. Each switching circuit 314 can optionally switch a right-leg-drive (RLD) signal 316 to the corresponding switchable lead connection 302 making that lead an output signal instead of an input signal. This is an advantage in a reduced lead set situation.

Continuing with FIG. 3, there are 5 signal preamps 126 (2 are not shown). Each switching circuit 314 can switch the signal input of a signal amplifier to one of five configurations as follows:

1. A switchable lead connection 302.
2. An analog ground 324.
3. A resistor 326 to analog ground.
4. A switchable input connection 302 and resistor 326 to analog ground.
5. A calibration voltage (CAL IN) 328.

Current sources 321 provide a leads-off signal which is used to determine whether a lead is making adequate contact with the patient. The magnitude of the leads off current is determined by an external resistor 322 to analog ground. The leads-off current sources 321 may be switched on or off by a switch 323. One switch controls all five channels. Input lead switching is discussed in detail in section VI in conjunction with FIG. 14.

The calibration voltage (CAL IN) 328 is driven by external amplifiers 330 which in turn combine 2 signals driven by two separate 6-bit sections of an internal calibration digital-to-analog converter (D/A) 332. The calibration voltage 328 is attenuated by an attenuator 329 to generate a preamp calibration voltage 320. Attenuator 329 is controlled by preamp gain signals so that as preamp gain is changed, the preamp calibration voltage 320 is automatically proportionally attenuated. There is also a special mode in which the calibration signal is a 1 mV pulse.

Outputs from each preamp 126 go to an averaging circuit 122. Averaging (summation) of signals subtracts any differential mode signals, leaving only common mode signals. The common mode averaging circuit output 336 (RLD OUT) is amplified by an external inverting integrator 124. The inverted amplified average signal, is used to subtract common mode signals at the patient (right-leg-drive). The external amplifier 340 may go to a separate external lead as illustrated in FIGS. 1 and 2, or may be routed back into the Chip (FIG. 3, 316, RLD IN) for switching to any of the 5 input signal leads. The averaging circuit 122 is discussed in detail in section V in conjunction with FIG. 13.

Physiological signals may have very low frequencies of interest. Therefore, a direct coupled signal path is desirable. Accordingly, the input amplifiers 126 within the Chip are direct coupled. However, a general problem with direct coupling is that amplification of any DC offset can saturate later amplifier stages. In the preferred application of the present invention, common mode feedback to the source (right leg drive) removes some DC offset. After DC amplification, additional offset subtraction is accomplished within the analog to digital conversion process described below.

Continuing with FIG. 3, each channel has an analog to digital (A/D) converter 346. The A/D conversion circuitry is discussed in detail in section III in conjunction with FIGS. 7-10. Each A/D converter 346 output goes to a single output data controller 348 for combined digital serial data output 350. Also illustrated is a data in signal 352 for serial chaining of Chips. Data in signal 352 and serial chaining is discussed further in section VIII below.

Each A/D converter 346, the calibration D/A 332, and an impedance current source 360 (discussed below) is connected to a reference voltage ($V_{REF}$) 331. The reference voltage 331 can be strapped to an internal band-gap voltage reference circuit (not illustrated) or it may be supplied externally.

Figure 15:
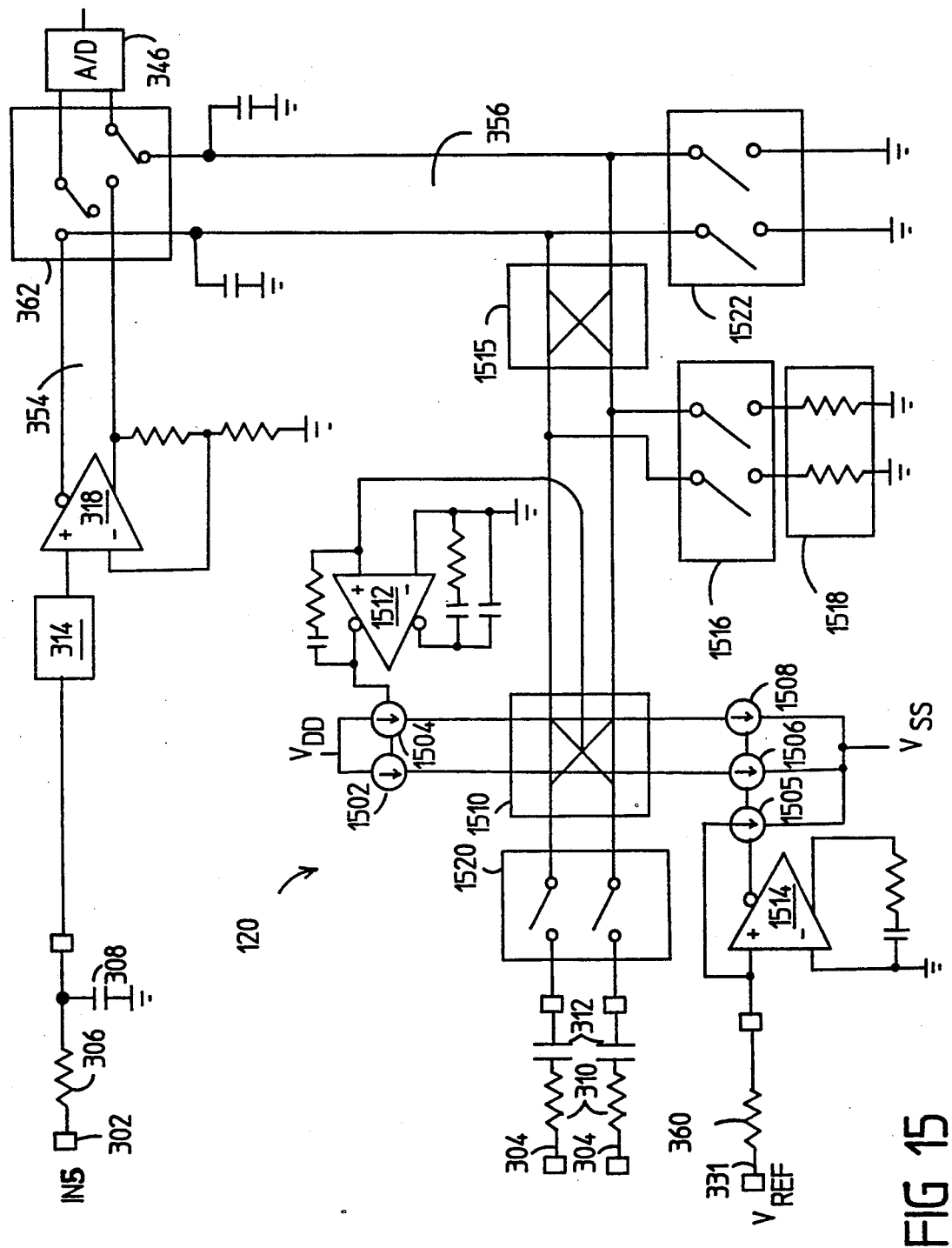
FIG. 15 is a block diagram illustrating additional detail for the AC impedance measurement circuitry illustrated in FIG. 3.
Figure 16A:
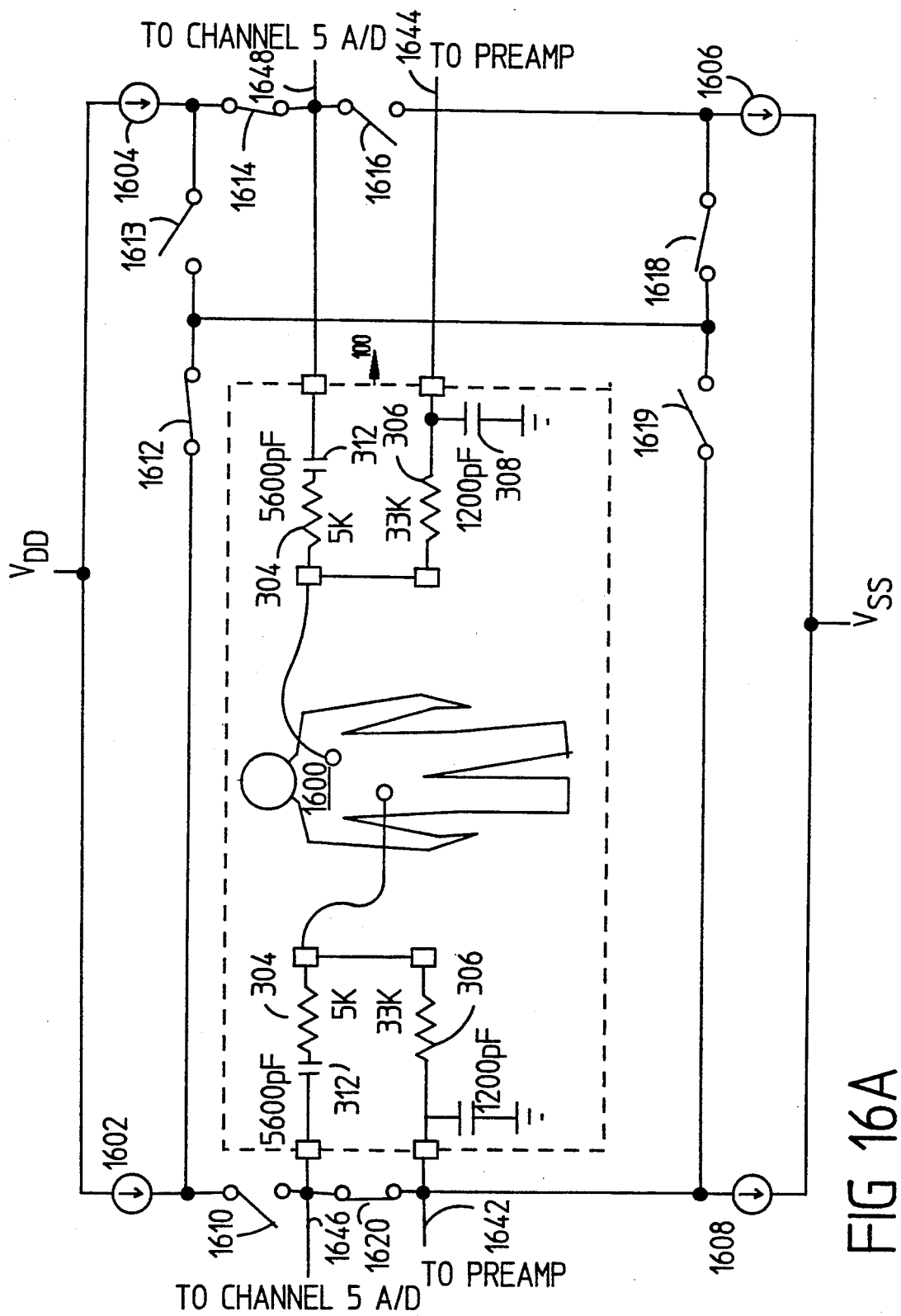
FIGS. 16A and 16B are simplified functional schematics illustrating alternating states of the AC impedance measurement circuitry illustrated in FIGS. 3 and 15.
Figure 16B:
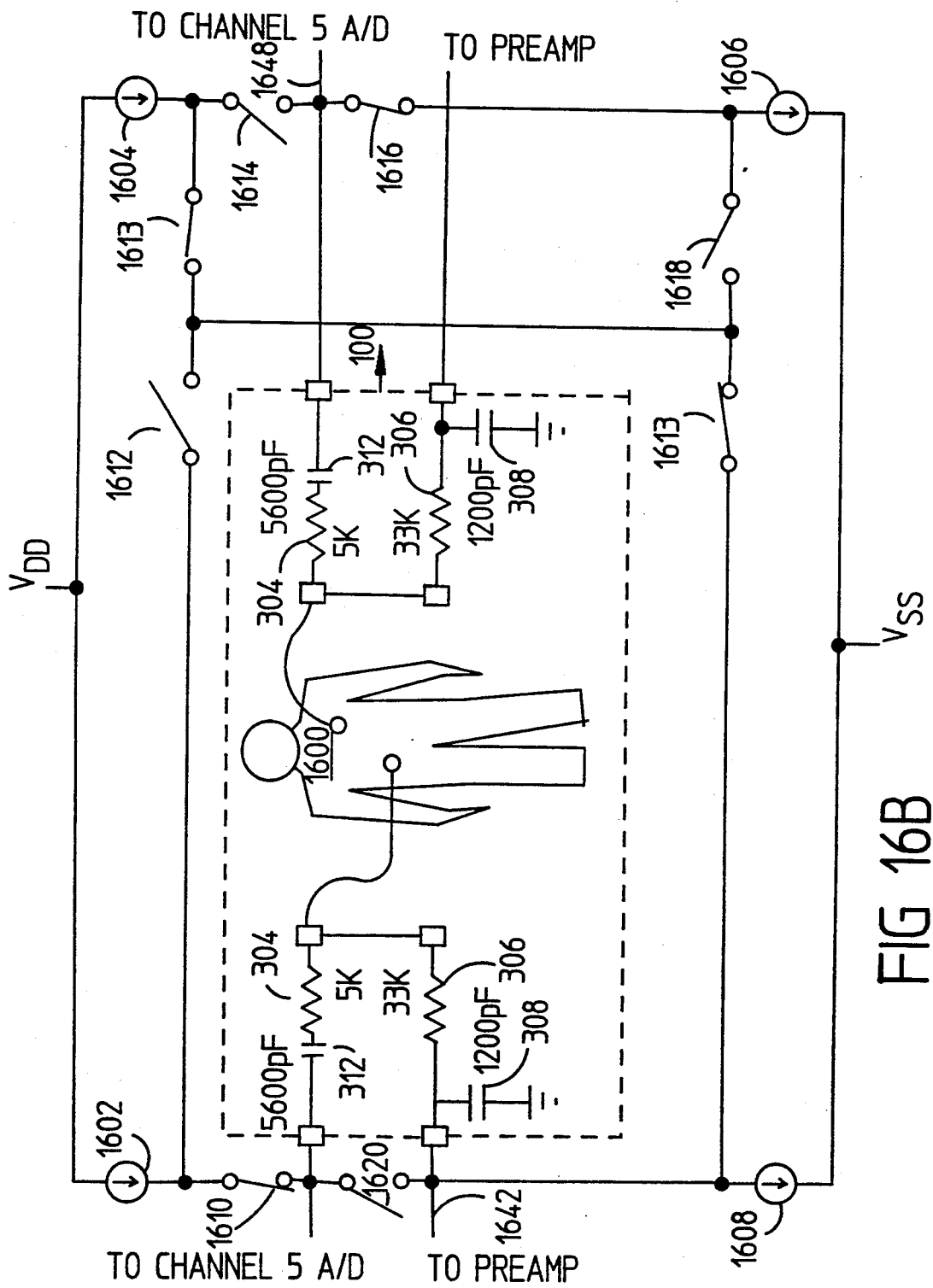
Figure 17:
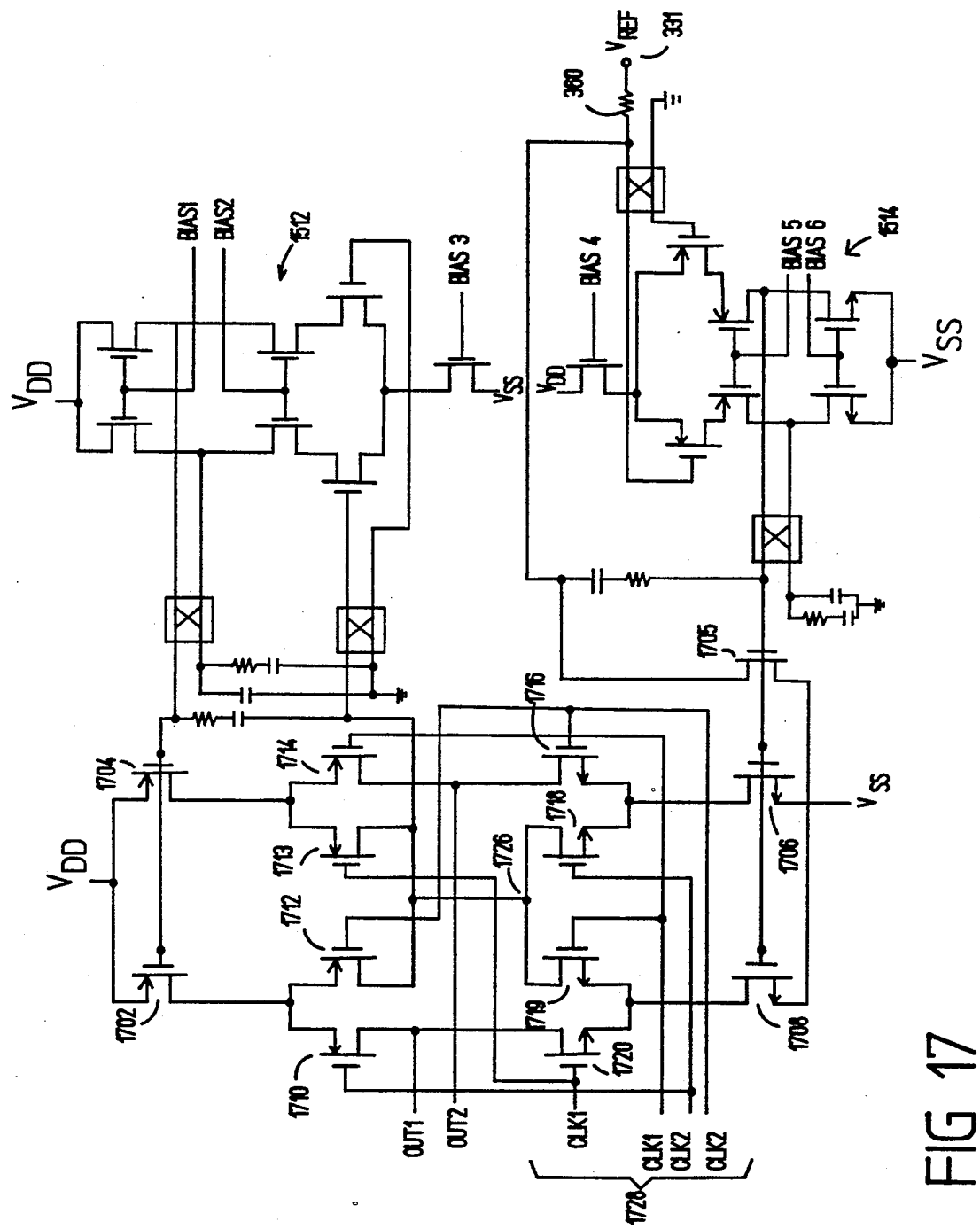
FIG. 17 is a simplified schematic illustrating additional detail of impedance measurement current sources illustrated in FIGS. 3, 15 and 16.

AC impedance measurement circuitry 120 (also FIGS. 1 and 2, 120) includes current sources (illustrated in FIGS. 15 and 17). The amplitude of the impedance current sources is controlled by an external resistor 360 to the reference voltage ($V_{REF}$) 331. The outputs of the impedance measurement circuitry 120 go to A/D input selection switches 362. The A/D selection switches 362 select a differential preamp output 354 or a differential impedance signal 356 to be converted by an A/D converter 346 for the fifth channel. The impedance measurement circuitry is discussed in detail in section VII in conjunction with FIGS. 15-17.

Note that the Chip could be implemented with multiple impedance measurement circuits, each with a dedicated A/D converter. However, in the preferred embodiment, a single impedance circuit shares an A/D converter with a preamp.

FIG. 3 also illustrates a box labeled digital control circuitry 364. Throughout the discussion below, reference will be made to digital control or programmable control. The digital control circuitry 364 provides this control. It is discussed in detail in section IX in conjuction with FIG. 19 and Appendices 1-4. The digital control circuitry 364 receives external serial digital data and commands from a control signal input 366. The Chip is designed to operate in a stand alone mode after input commands have been entered.

The digital control circuitry 364 is also connected to two external address connections 368. As mentioned above, up to six Chips can be connected together in a serial chain. Each serially chained device may have one of four digital addresses. This is accomplished by externally forcing address connections 368 to combinations of logical "0" or logical "1". External commands are then directed to a specific address. If more than four devices are serially chained, at least two devices must have the same address. Serial chaining is discussed in detail in section VIII in conjunction with FIG. 18.

The Chip has a clock circuit 370 containing an oscillator circuit which can be used with an external crystal 372 as illustrated. Alternatively, an external clock may be used in place of the crystal. Although not explicitly illustrated in FIG. 3, other clock signals are derived from the output of clock 370 and used throughout the chip. These derived clocks will be illustrated or implied below in conjunction with chopper stabilized amplifiers, switched capacitor resistor implementations, analog-to-digital conversion, digital-to-analog conversion, and other circuitry throughout the Chip.

There is also a provision for initial synchronization of the A/D conversion cycle and serial data output to external events (SYNC IN, 373). If multiple Chips are serially connected, one Chip may provide the master clock for other chips (SYS CLOCK OUT, 374). A master/slave connection 369 designates whether a Chip is to generate its own clock or receive an external clock from a master Chip.

II. ANALOG INPUT AMPLIFIERS

As discussed in the background section, physiological signals must be extracted from noise. In addition to noise external to the amplifier, there are typically significant internal sources of noise such as the front-end of the first stage of amplification, switching noise from digital circuitry, and power supply noise. In the present invention, amplifier front-end noise is reduced by chopping. Internal switching noise and power supply noise are reduced by making the analog channel differential and by using common-mode feedback at every stage of amplification.

Figure 4A:
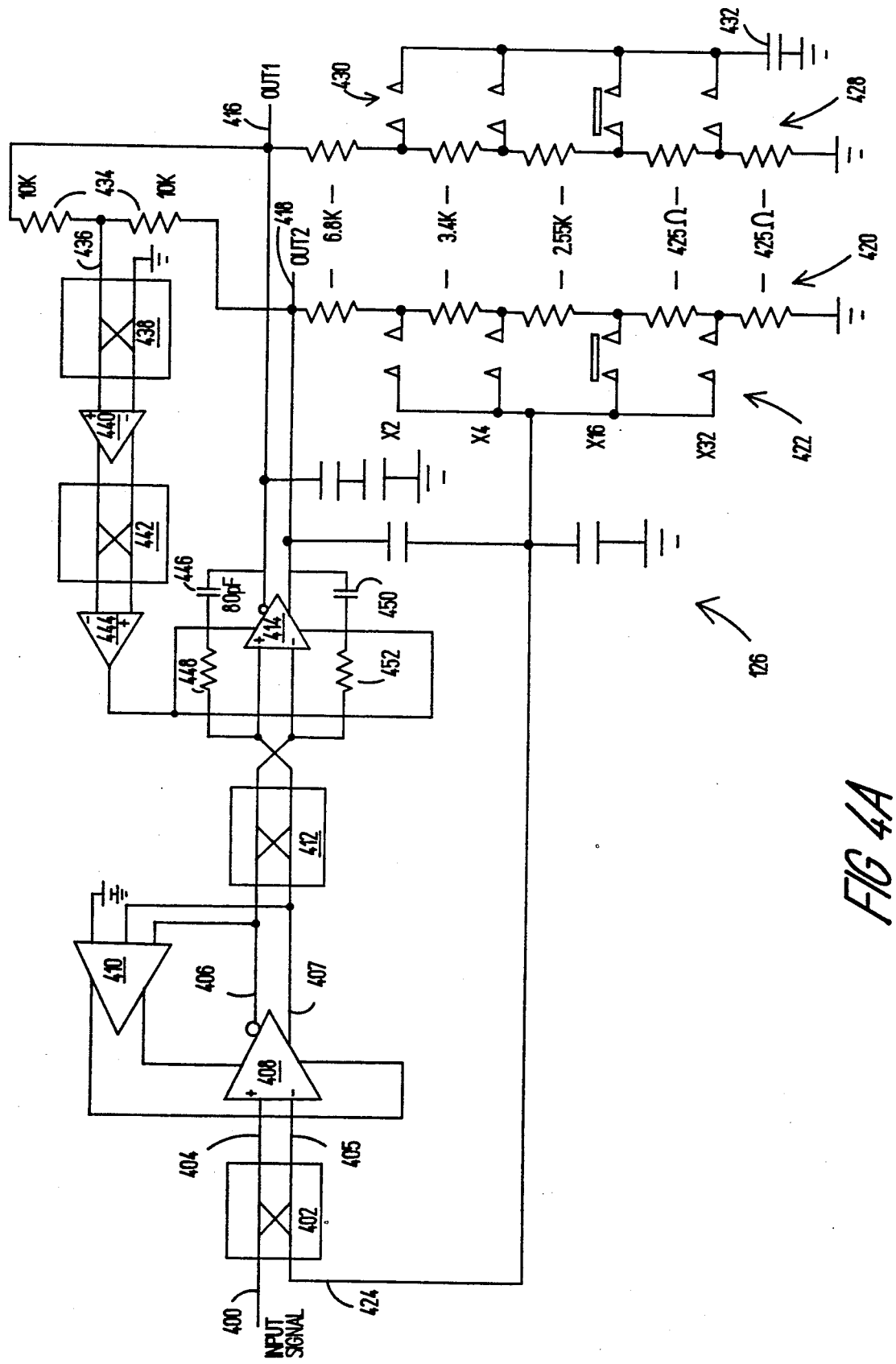
FIG. 4A is a more detailed block diagram of an analog preamplifier illustrated in FIG. 3.

FIG. 4A illustrates additional detail of a preamp (FIGS. 1, 2 and 3, 126) as implemented in the preferred embodiment of the Chip. As an overview, there is a chopper 402 followed by a first stage amplifier 408. The outputs of the first stage amplifier 408 are added in a first stage common mode feedback amplifier 410 which has two separate feedback paths. The outputs (406, 407) of the first stage amplifier 408 are chopped by a second chopper 412 before being amplified by a second stage amplifier 414. The second chopper 412 is in phase with the first chopper 402. The result at the output of the second chopper 412 is synchronous rectification of the amplified differential inputs (signal 400 and the amplified feedback signal 424). The second stage amplifier 414 has a chopper stabilized common mode feedback amplifier (438, 440, 442 and 444). A resistor ladder 420 with an electronic switch 422 provides programmable selection of overall closed loop gain.

Analyzing FIG. 4A in more detail, an input signal 400 and a negative feedback gain signal 424 are chopped by a first chopper 402 before being amplified by a first stage differential amplifier 408. Chopper 402 conceptually switches back and forth between the configurations depicted in FIGS. 4B and 4C. When the first chopper 402 in FIG. 4A is in the configuration depicted in FIG. 4B, the input signal 400 in FIG. 4A is connected to a first input 404 of first stage amplifier 408 and the feedback signal 424 is connected to a second input 405 of the first stage amplifier 408. When the first chopper 402 in FIG. 4A is in the configuration depicted in FIG. 4C, the input signal 400 in FIG. 4A is connected to the second input 405 of first stage amplifier 408 and the feedback signal 424 is connected to the first input 404 of first stage amplifier 408.

As a result of chopping, the external input signal 400 passes alternately through each side of the first stage amplifier 408. Each side of the first amplifier 408 has some offset voltage and some 1/f noise. The offset voltages and 1/f noise have a common mode portion and a differential portion. The common mode portion is reduced by the amplifier's (408) differential input stage and is further detected and subtracted by the first stage common mode feedback amplifier 410 which is discussed below. The differential portion is reduced by chopping, synchronous rectification and averaging as follows. After an input signal 400 is chopped, amplified alternately by each side of the first stage amplifier 408 and synchronously rectified by the second chopper 412, the result is an amplified input signal with a superimposed square-like wave. The peaks of the superimposed square-like wave result from the amplified differences in offset voltage and 1/f noise between the two sides of the first stage amplifier 408. If multiple cycles of the superimposed square wave are averaged (for example, by low pass filtering), the result is an amplified input signal with most of the effects of offset voltage differences and 1/f noise differences averaged out.

In the Chip, there is low pass filtering (446, 448, 450 and 452) which is discussed below. In addition, in the Chip, the A/D converters are synchronized to the chopping signals. Each digital sample from an A/D converter averages an integral number of chopping cycles (typically 32) so that offset voltage differences and 1/f noise differences are further reduced by averaging. This is an advantage of continuous A/D conversion.

An alternative analysis of the effects of chopping may be made by analyzing the result in the frequency domain. The input signal is translated up to the chopper frequency, amplified, and translated back down to base band. The dominant noise source within the amplifier circuitry is the input devices in the first amplifier stage 408. Since these input devices are beyond the first chopper 402, the input device noise is amplified at baseband frequency by amplifier 408 while the input signal is amplified at the chopper frequency. The second chopper 412 can then be viewed as a modulator which returns the input signal down to base band but translates the amplified input noise up to the chopper frequency. This high frequency noise is then filtered out by a low pass filter and by an integrating A/D converter. In the preferred embodiment of the present invention, the chop frequency is 128 KHz.

Continuing with FIG. 4A, the second stage 414 of the preamp has a first output 416 and a second output 418. The second output 418 has a series of resistors 420 to ground. An electronic switch 422 selects a fraction of the second output 418 for negative feedback signal 424 which controls the overall preamp closed loop gain. In the preferred embodiment, with resistor values as shown in FIG. 4A, the gain can be selected to values of 2, 4, 16, and 32. The position of the electronic switch 422 illustrated in FIG. 4A results in a closed loop gain of 16. The position of the electronic switch 422 can be controlled by external digital signals which are discussed below in section IX.

As illustrated in FIG. 4A, outputs 416 and 418 have symmetrical loading. A resistor network 428 and electronic switch 430 are identical to resistor network 420 and electronic switch 422, respectively, except the electronic switch 430 output just goes to a capacitive load 432.

As also illustrated in FIG. 4A, the outputs (416 and 418) of the second stage amplifier 414 have a center-tapped pair of resistors 434 connected between the outputs (416 and 418). The center-tap provides a common mode output signal 436 which is the average of the two outputs (416 and 418). The common mode output signal 436 is chopped (438), amplified (440), synchronously rectified (442), further amplified (444) and a single resulting signal is subtracted from each side of the second stage amplifier 414.

Continuing with FIG. 4A, the second stage amplifier 414 has a series capacitor 446 and resistor 448 from the first output 416 to a first input and a series capacitor 450 and resistor 452 from the second output 418 to a second input. These components provide a low pass filter for the differential signal amplifier. These components are chosen to provide the dominant pole (approximately 3 Hz) for the overall preamp frequency response to ensure overall closed loop preamp stability. This is accomplished by Miller effect amplification of the feedback capacitors (446 and 450). The series resistors (448 and 452) provide a zero in the amplifier frequency response for fine adjustment of the response near the frequency where gain is equal to one.

Figure 4C:
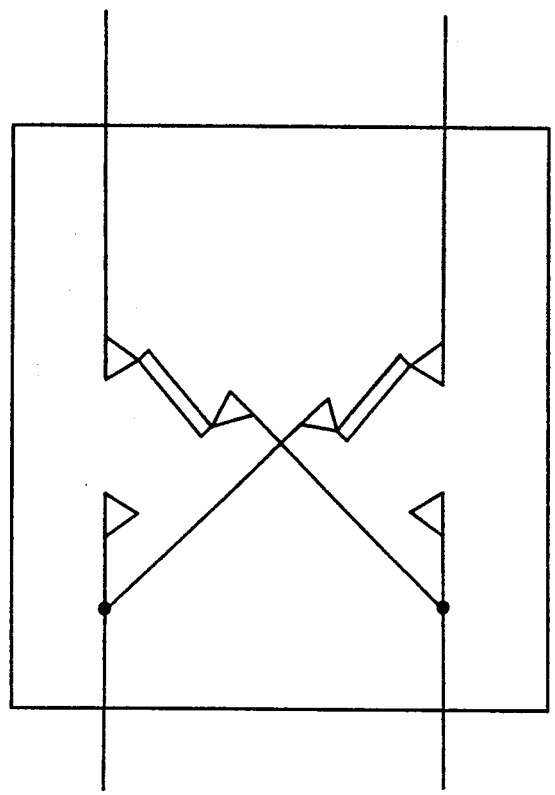
FIGS. 4B and 4C are detailed functional illustrations of configurations of choppers illustrated in FIG. 4A.
Figure 4B:
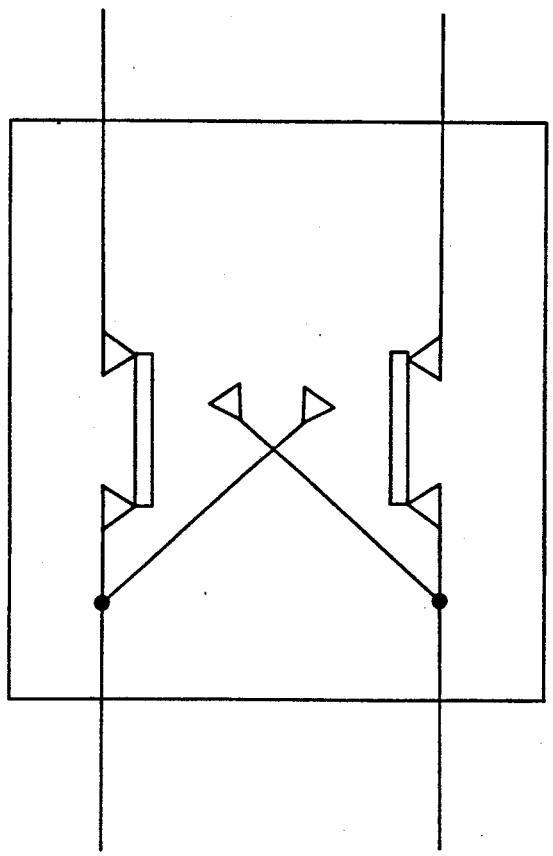
Figure 5:
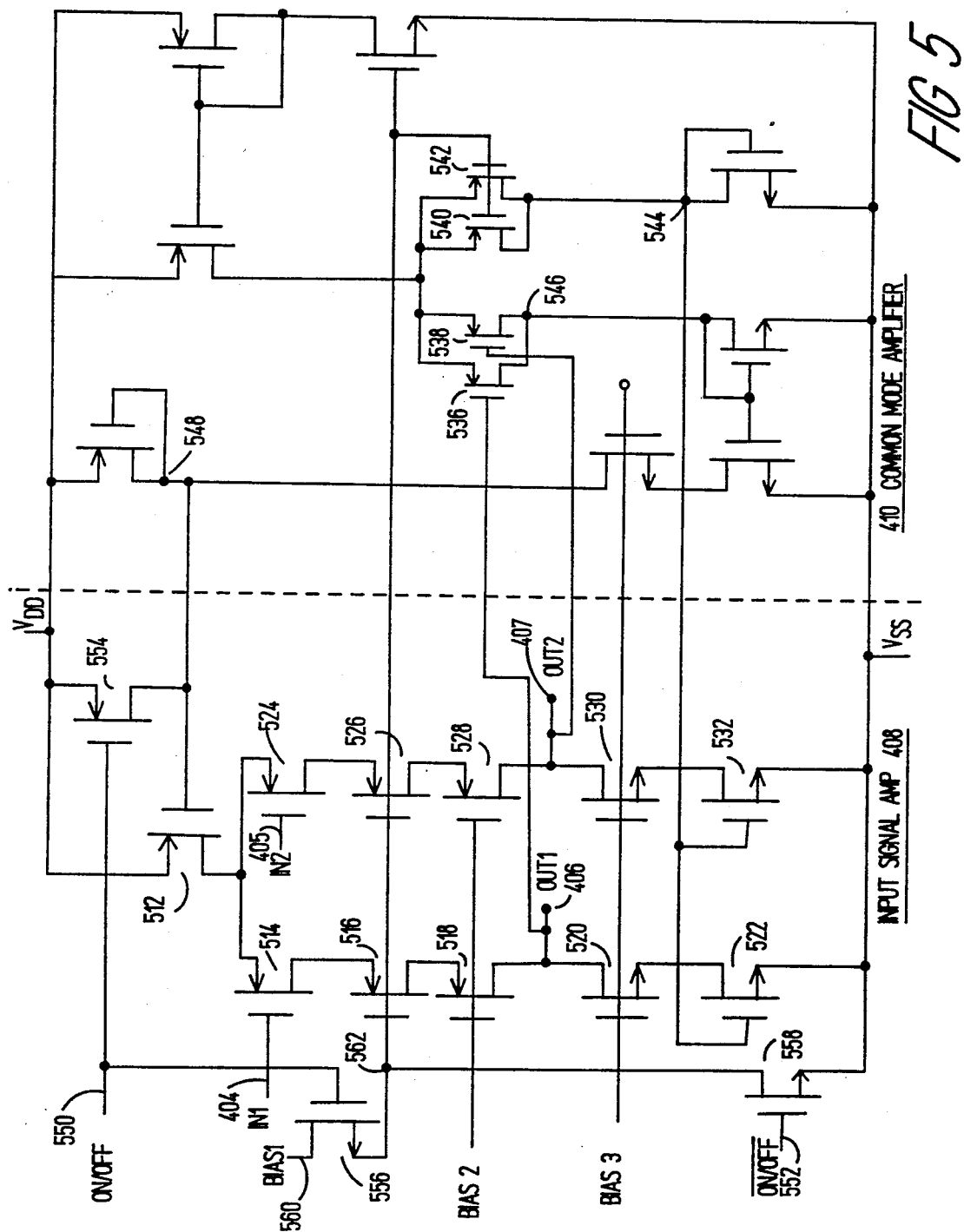
FIG. 5 is a more detailed schematic of the first amplification stage of the analog preamplifier illustrated in FIG. 4A.

FIG. 5 illustrates additional detail for the first stage of the signal amplifier (FIG. 4, 408) and its common mode feedback circuitry (FIG. 4, 410). FIG. 5 is divided into two parts by a vertical dashed line. The basic signal amplifier 408 is illustrated on the left side of the dashed line. The common mode feedback circuitry 410 is illustrated to the right of the dashed line. The signal amplifier 408 has two input signals (404 and 405) (also FIG. 4, 404 and 405) and two output signals (406 and 407) (also FIG. 4, 406 and 407).

PMOS transistor 512 serves as a common bias current source for the signal amplifier 408. The first input signal 404 is amplified by a PMOS transistor 514. The output load for PMOS transistor 514 is a cascode arrangement of two PMOS transistors (516 and 518). An NMOS current source 522 also has a cascode device 520 to increase the impedance of the output 406. Likewise, the second input signal 405 is amplified by transistor 524 with a two transistor cascode load (526 and 528) along with a current source 532 and cascode device 530. The input signal transistors 514 and 524 are PMOS for superior 1/f noise characteristics relative to NMOS. The open loop gain of the signal amplifier 408 is proportional to the transconductance ($g_m$) of transistor 514 (or transistor 524) times the output impedance. Transistors 514 and 524 are fabricated with large widths to maximize transconductance. However, this also reduces the output impedance. Therefore, a double cascode arrangement is used to implement very high output impedance. Transistors 516 and 518 (and 526 and 528) have short channel lengths (1 micrometer) for faster transit times than a single longer device. The overall result is an input stage with high input impedance, low 1/f noise, fast pulse response and very high open loop gain (typically greater than 70 dB). The high open loop gain of the first stage helps minimize the effects of 1/f noise of the second stage.

The double cascode arrangement illustrated in FIG. 5 ((516, 518, 520 and 522) and (526, 528, 530 and 532)) is less complex than folded cascode circuits typically used in similar applications. The restricted range of input signals allows this improved design.

Continuing with FIG. 5, the common mode feedback amplifier 410 is also a differential amplifier. The input signal amplifier outputs (406 and 407) are parallel inputs (transistors 536 and 538) on one side of the common mode amplifier 410. The other input transistors (transistors 540 and 542) of the common mode amplifier 410 are biased by a constant voltage 562. The noninverted output 544 of the common mode amplifier 410 is used as a feedback to two load transistors (522 and 532) for the input signal amplifier 408. The inverted output 546 of the common mode amplifier 410 is amplified and offset and used as a feedback voltage 548 to the common current source 512 for the input signal amplifier 408.

For illustration of the common mode feedback mechanism, assume output signal 1 (406) and output signal 2 (407) both increase. The common mode input transistors 536 and 538 conduct less, causing the common mode inverted output 546 to fall. This causes the feedback voltage 548 to rise. This causes the input signal amplifier common current source bias transistor 512 to conduct less current which finally causes output voltages 406 and 407 to fall. Likewise, the common mode noninverted signal 544 rises, causing input signal amplifier load transistors 522 and 532 to conduct harder, which reduces the output signals 406 and 407.

Also illustrated in FIG. 5 is an ON/OFF signal 550 and an inverted ON/OFF signal 552. Digital control circuitry (FIG. 3, 364) can turn each channel on or off. Transistors 554, 556 and 558 provide this capability for each first stage amplifier. In the amplifier "off" condition, transistor 554 is "on", shorting out the gate voltage for the common bias current source transistor 512. In addition, transistor 556 is "off" and transistor 558 is "on", forcing a bias line 562, which is used in all amplifier stages, to one supply voltage.

Figure 6:
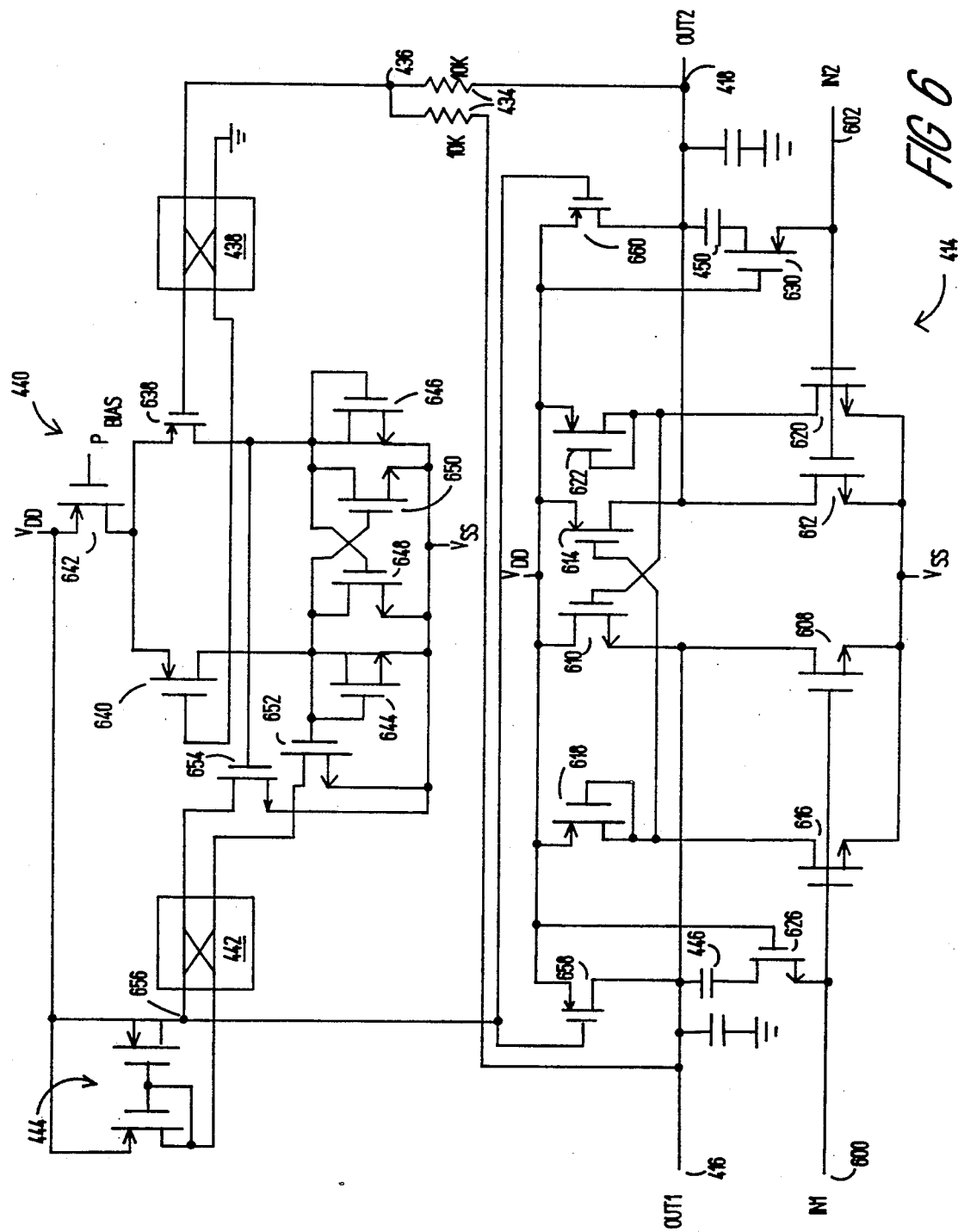
FIG. 6 is a more detailed schematic of the second amplification stage of the analog preamplifier illustrated in FIG. 4A.

FIG. 6 illustrates additional detail for the second stage of the preamp (FIG. 4, 414) and its associated common mode feedback amplifier (FIG. 4, 438, 440, 442 and 444). As illustrated in FIG. 6, the differential second stage amplifier has a first input signal 600, a second input signal 602, a first output signal 416 and a second output signal 418. A series capacitor 446 and a transistor biased as a resistor (626) (corresponding to FIG. 4, resistor 448) are connected between the first output 416 and the first input 600. Symmetrically, capacitor 450 and a transistor biased as a resistor (630) (corresponding to FIG. 4, resistor 452) are connected between the second output 418 and the second input 602. These components provide low pass filtering as discussed with FIG. 4.

The first input signal 600 is amplified by transistor 608 which has two variable current source loads (610 and 658). Symmetrically, the second input signal 602 is amplified by transistor 612 which has two variable current source loads (614 and 660). Variable loads 658 and 660 are controlled by a separate common mode feedback amplifier which is discussed below.

Variable load 610 for the first input signal 600 is controlled by the output of a separate amplifier for the second input signal 602 (transistor 620 with fixed current source load 622). Transistors 622 and 610 form a current mirror circuit. Symmetrically, variable load 614 for the second input signal 602 is controlled by the output of a separate amplifier for the first input signal 600 (transistor 616 with fixed current source load 618). Transistors 618 and 614 also form a current mirror circuit. This cross coupling of outputs provides reduced gain for common mode signals and increased gain for differential signals. As a result, the common mode rejection ratio is increased.

The first output signal 416 and second output signal 418 are connected to a resistor pair 434 (also FIG. 4, 434). The resistor center tap, common mode signal 436 (also FIG. 4, 436), is the average of the two outputs (416 and 418). Common mode signal 436 and analog ground are then chopped by a first chopper 438 (also FIG. 4, 438). The chopped signals are then amplified by transistors 640 and 638 which have a common bias current source 642. Transistors 640 and 638 have a combination of diode connected FET loads (644 and 646) and cross coupled variable current source loads (648 and 650). The cross coupled loads (648 and 650) increase common mode rejection ratio.

FIG. 6, transistors 638–654 correspond to amplifier 440 in FIG. 4. The feedback amplifier outputs (from transistors 652 and 654) are synchronously rectified by a second chopper 442 (also FIG. 4, 442). The outputs of the second chopper 442 are connected to a P-channel current mirror circuit 444 (also FIG. 4, 444), which provides feedback signal 656. Feedback signal 656 controls variable loads 658 and 660 to reduce the common mode signal on output nodes 416 and 418.

III. ANALOG TO DIGITAL CONVERSION

In the Chip, the analog to digital conversion circuits are a novel implementation combining features of two classes of A/D conversion known as closed loop pulse width modulated conversion and sigma-delta modulation conversion with the ability to switch the conversion mode to either class. Other novel features of the A/D circuits include an autoranging offset subtraction circuit and a programmable tradeoff between resolution and bandwidth.

As background, in a basic pulse-width-modulated A/D converter, a signal to be digitized is one input to an analog comparator and the reference input to the comparator is a triangular waveform. When the input signal is more positive than the triangular waveform, the output of the comparator is high. Otherwise, the output of the comparator is low. The resulting comparator output is a series of pulses with a frequency equal to the frequency of the triangular waveform and the width of each pulse is proportional to the amplitude of the input signal. A triangular waveform may be implemented by integrating a square wave. Therefore, a refinement of the basic comparator circuit is to use an integrating amplifier both to generate a triangular waveform from a square wave and to filter the input signal.

Figure 7:
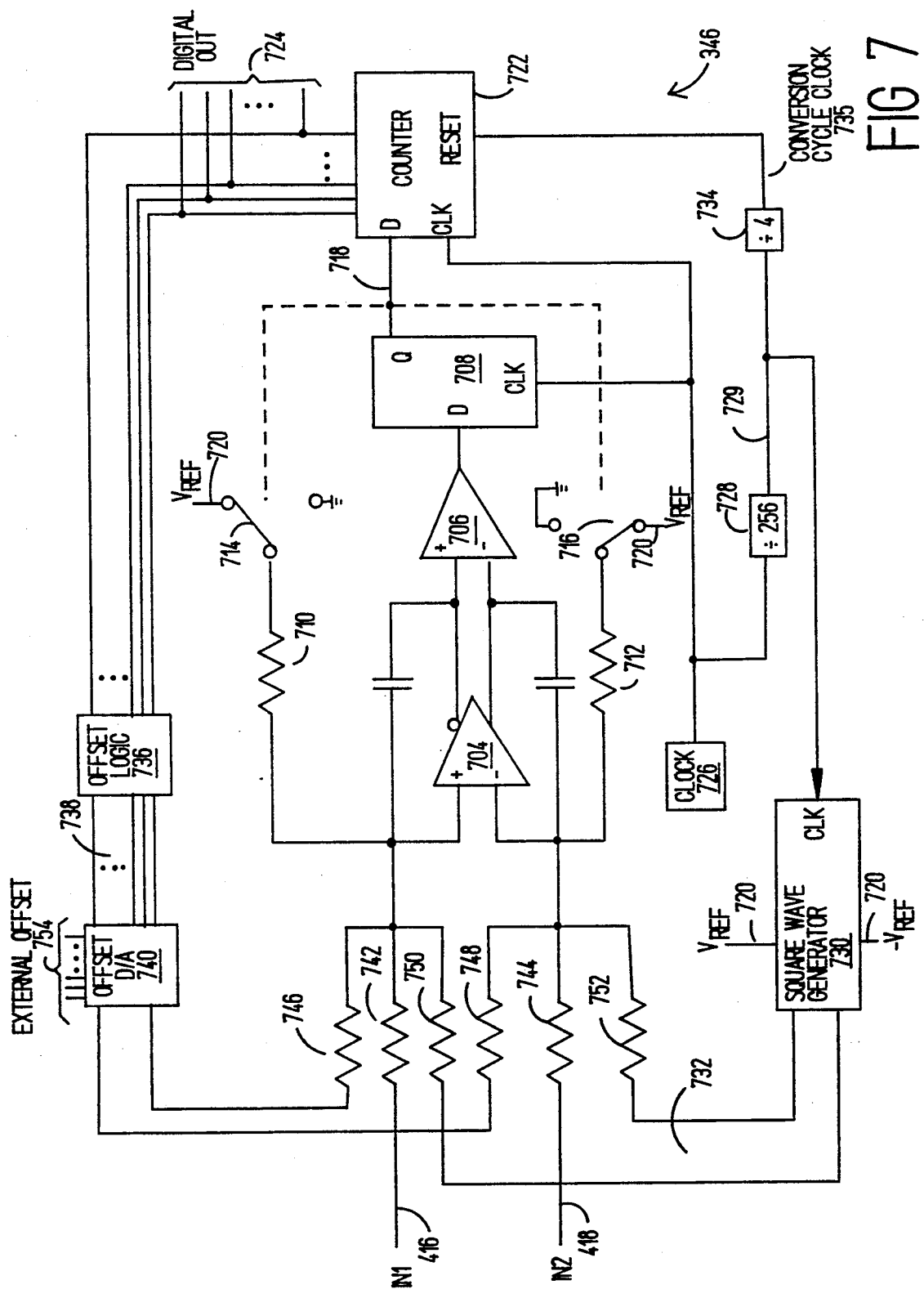
FIG. 7 is a block diagram of the analog to digital converter illustrated in FIG. 3.

FIG. 7 illustrates a closed loop pulse width modulated A/D converter as implemented in the Chip. The A/D converter illustrated in FIG. 7 is differential. Therefore, there are two differential signal inputs (416 and 418, corresponding to preamp outputs, FIG. 4, 416 and 418). An operational amplifier 704 with feedback capacitors operates as an integrator for a differential (complementary) square wave 732 and also serves as a low pass filter for the inputs (416 and 418). The combined triangular wave (integrated square wave) and filtered input signals are compared by comparator 706. The output of the comparator 706 is a series of pulses with a frequency equal to the frequency of the square wave 732 and widths proportional to the difference between the input signals (416 and 418). A clocked flip-flop 708 is used to precisely synchronize pulse edges to edges of a first clock 726. The synchronized output 718 is used to control reference switches (714 and 716) that provide a precise voltage feedback back to the input. Feedback resistors (710 and 712) ensure that the average value of the synchronized pulses is equal to the average value of the differential input signal (multiplied by the closed loop gain). Digital counter 722 counts clock pulses during the period that the output 718 of the flip-flop 708 is high, thereby measuring the width of pulses from flip-flop 708.

The frequency for the first clock 726 is externally controllable. Two dividers (728 and 734) generate two lower frequency clock signals (729 and 735 respectively). The value for each divider (728 and 734) is also programmable. The values in the following discussion are example values appropriate for the Chip when used in an ECG application. In an ECG application, the first clock 726 is typically 4.096 MHz. This first clock is used to synchronize flip-flop 708 and is also used as the clock (count) input for the counter 722. The first divider 728 typically divides the 4.096 MHz clock (726) by 256 to provide a 16 Khz clock (729) for the square wave generator 730. The second divider (734) typically divides by 4 to provide a 4 KHz reset signal (conversion cycle clock 735) to the counter 722, thereby controlling the overall conversion rate. As a result, the counter 722 is reset every 1,024 ($2^{10}$) clock pulses. Therefore, for these values, counter 722 provides 4,000 10-bit digital samples per second.

As discussed with FIG. 5, the chop frequency for all choppers is 128 KHz. Therefore, for the above values, each counter update averages 32 chop periods, thereby reducing any remaining chopper noise. In addition, note that the frequency of the square wave generator 732 is four times the frequency of the counter reset signal so that each counter update is the total width of four pulses from the flip-flop 708. Therefore, noise is reduced by averaging multiple pulses. Also, note that for ECG applications, the signals of interest are less than 200 Hz. An A/D sample rate of 4,000 samples per second is 10 times the Nyquist rate of 400 samples per second. Therefore, the A/D converter is an oversampling converter and an external microprocessor can average consecutive samples, digitally filter the digital samples, or perform other digital signal processing for additional noise/bandwidth tradeoff.

As discussed above, the value of the dividers (728 and 734) illustrated in FIG. 7 are typical values appropriate for electrocardiograph application. However, the dividers (728 and 734) are programmable and can be changed by the digital control circuitry (discussed below in section IX). For example, the second divider 734 can be programmed to divide by 16. The conversion cycle clock 735 then provides a 1 KHz reset signal to counter 722. The counter 722 then provides 1,000 12-bit digital samples per second. Therefore, in the preferred embodiment, there is a programmable tradeoff between bandwidth and resolution. The programmable range for bits/sample is from 9 bits/sample to 14 bits/sample (corresponding to 8,000 samples/sec to 250 samples/sec respectively).

Continuing with FIG. 7, the square wave generator 730 can be turned on or off by a digital control signal (discussed below in section IX). If the square-wave generator 730 is turned off, the circuitry illustrated in FIG. 7 functions as an alternative class of A/D converter known as a sigma-delta modulator. In a sigma-delta modulator, a comparator compares an integrated input to a reference voltage. The polarity of the reference voltage depends on the output of the comparator. In FIG. 7, the reference voltage feedback switches (714 and 716) are functionally equivalent to switching a reference voltage polarity.

For either mode of A/D (sigma-delta modulator or closed loop pulse width modulator), feedback to the integrating amplifier 704 assures an output 718 which has an average value equal to the negative of the average value of an input signal (700 and 702) difference. Counting clock pulses 726 during the periods the output 718 is high yields a digital equivalent 724 of the analog input (416 and 418) difference. The primary difference in operation is that the frequency of the synchronized comparator output 718 in the sigma-delta modulator mode is not locked to the frequency of the square wave 732. As a result, as implemented in the present invention, transient response times and transient settling times are faster in the sigma-delta modulator mode than in the closed loop pulse width modulator mode. However, there is a tradeoff in that noise levels are higher in the sigma-delta modulator mode than in the closed loop pulse width modulator mode. Again, either mode can be selected by turning the square-wave generator 730 on or off.

Further illustrated in FIG. 7 is an offset subtracting digital to analog (D/A) converter 740. The D/A converter 740 may be controlled by externally supplied values 754 or by internal logic control 736. If internal logic control 736 is selected, the digital outputs 724 of the counter 722 are monitored by offset logic 736. If the value of the A/D digital output 724 exceeds a programmable threshold for a programmable number of A/D counter samples, a bi-directional offset value 738 within the offset logic 736 is incremented. The D/A converter 740 then generates differential offset voltages to subtract from the input signals 416 and 418. Offset resistors 746 and 748 are depicted as single resistors for simplicity of illustration but are actually D/A resistor networks (illustrated in FIG. 10).

Each serial digital A/D output value from the Chip to an external microprocessor includes one bit of offset information. The direction of change associated with the single bit of offset data may be inferred from previous A/D output values. Therefore, an external microprocessor can update an external register to keep track of the offset value. Alternatively, the Chip may be commanded to output the offset D/A (740) values instead of the A/D (724) values. As a result, the effective range of the A/D converters is extended by the number of bits of offset.

The analog value of one least significant bit from the A/D counter 722 varies with gain and resolution. The analog value of one least significant bit to the offset D/A 740 is fixed at 32 mV on each of the differential inputs (at resistors 746 and 748), relative to IN1 (416) and IN2 (748).

Figure 8:
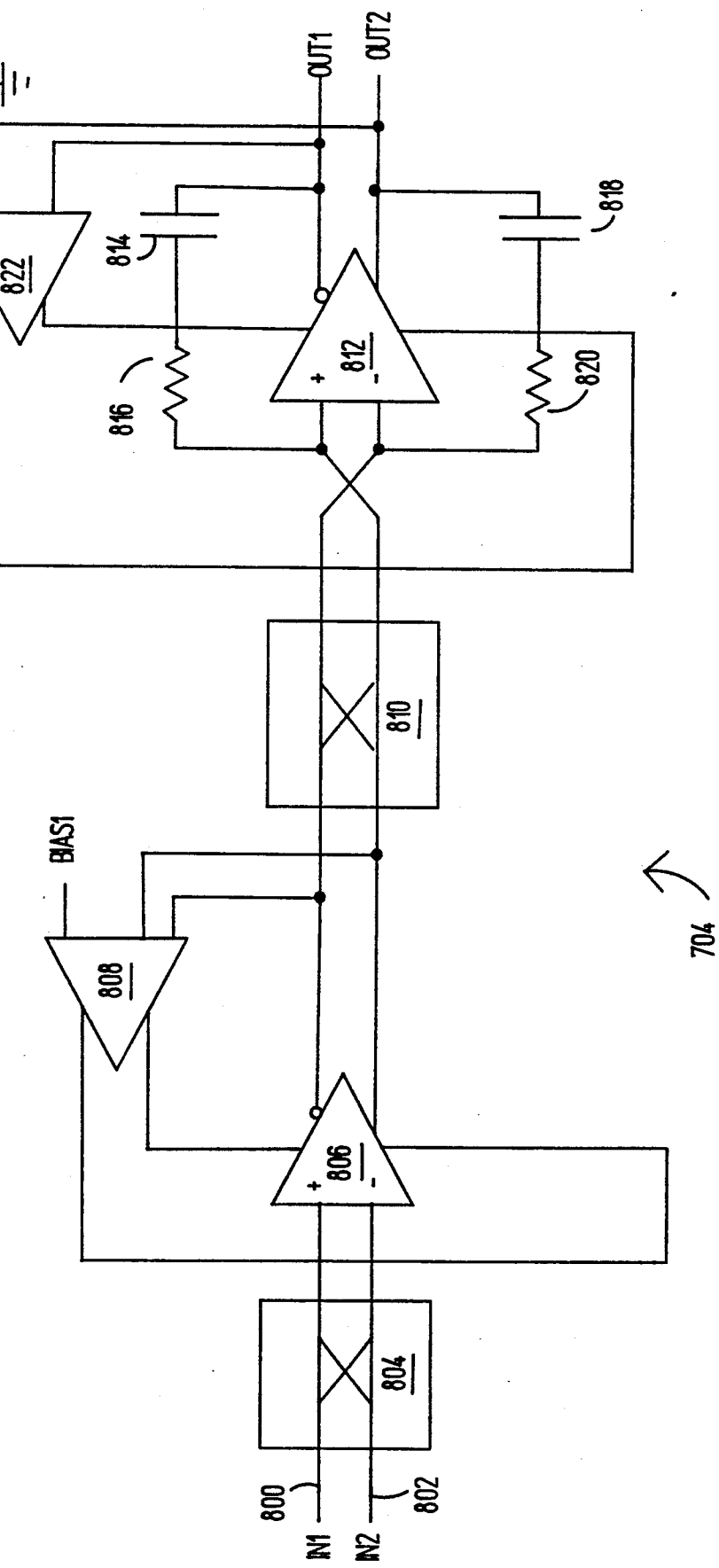
FIG. 8 is a more detailed block diagram of an amplifier within the A/D converter illustrated in FIG. 7.

FIG. 8 illustrates additional detail for the integrating amplifier within the A/D (FIG. 7, 704). As illustrated in FIG. 8, two differential inputs (800 and 802) are chopped by a first chopper 804, amplified by a first stage amplifier 806, which has a common mode feedback amplifier 808. A second chopper 810 synchronously rectifies the signals before amplification by a second stage amplifier 812. The second stage amplifier 812 also has a common mode feedback amplifier 822. The first stage amplifier 806 and its common mode feedback amplifier 808 are identical to the detailed schematic illustrated by FIG. 5. The second stage amplifier 812 and feedback amplifier 822 are similar to the detailed schematic illustrated by FIG. 6 except the feedback amplifier 822 is not chopper stabilized.

Figure 9A:
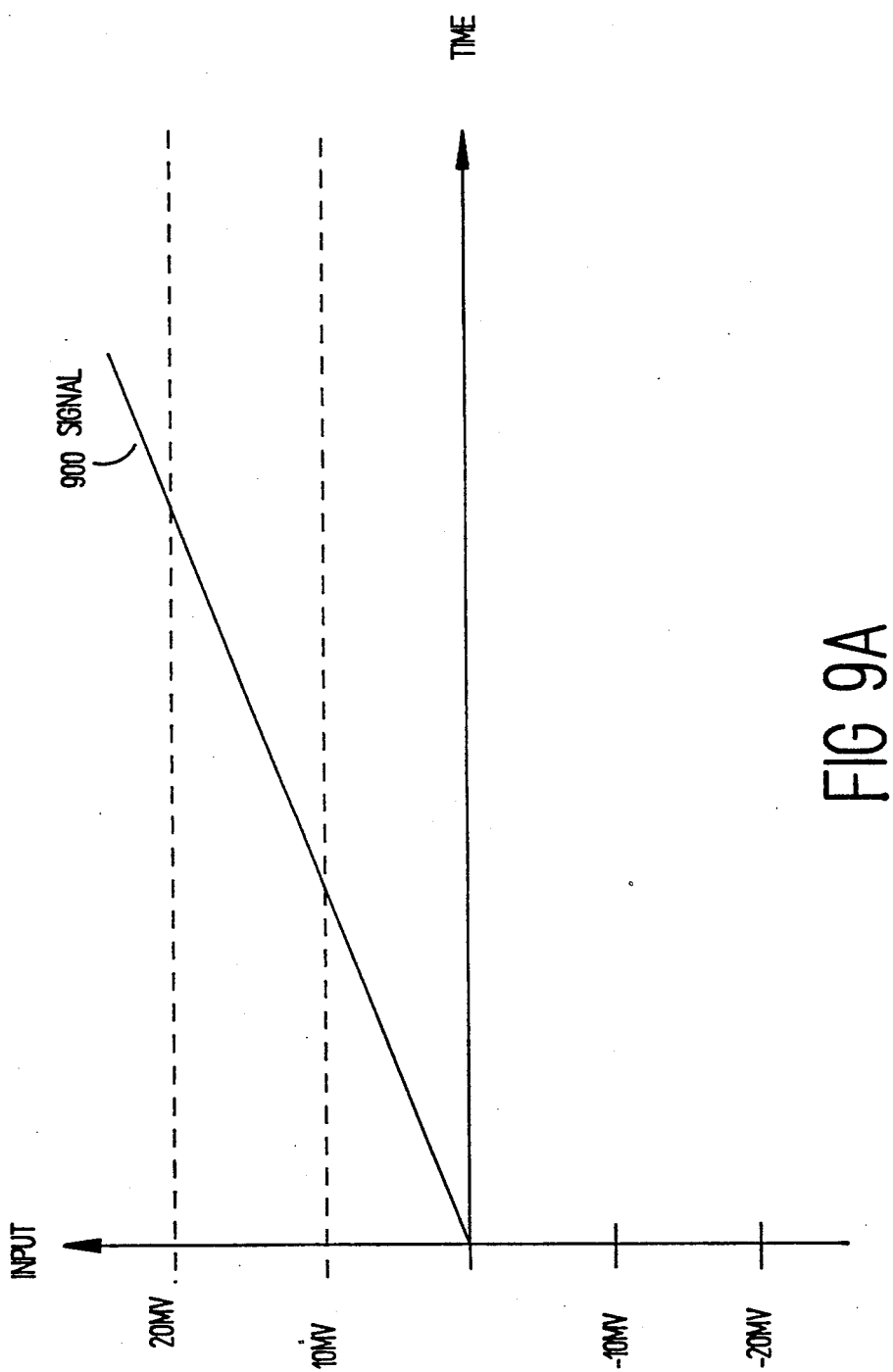
FIG. 9A is an example signal waveform to illustrate the function of the autoranging offset circuit within the A/D converter illustrated in FIG. 8.

FIGS. 9A-9C depict example waveforms to illustrate the overall function of the offset D/A (FIG. 7, 740) when the offset D/A is being controlled automatically by internal logic. All voltage values illustrated in FIG. 9 depict voltages reflected back to the preamp input (FIG. 4, 400) assuming a preamp gain of 4. When the preamp gain is 4, the maximum A/D input range is ±10 mV but the offset D/A permits the overall range to be ± 0.5 V. FIG. 9 uses a ±10 mV range as an example range to illustrate the offset function. However, other values of preamp gain would change the voltage thresholds illustrated.

FIG. 9A depicts an example input signal 900. The example input signal 900 linearly ramps in time from 0 volts to greater than 20 mV. As explained above, an input voltage of 10 mV, with no offset, will generate the maximum digital output value. Therefore, the input signal 900 exceeds the range of the A/D.

FIG. 9B depicts in analog fashion the effective value 902 of the A/D digital output (FIG. 7, 724). To the right of FIG. 9B is an expanded view of the ±10 mV output range (904 and 922) illustrating 4 pairs of symmetrical offset threshold voltages (906 and 920, 908 and 918, 910 and 916, 912 and 914). The threshold voltages correspond to ±50% (912 and 914), ±62.5% (910 and 916), ±75% (908 and 918), and ±87.5% (906 and 920) of the A/D output range (904 and 922). FIG. 9B depicts a result of setting the offset threshold at 75% (908 and 918) (±7.5 mV), with signal 900 (FIG. 9A) as an input.

FIG. 9C depicts the output 928 of the offset D/A (FIG. 7, 740). At time T1 (924), the A/D converter output 902 exceeds the positive threshold 908 (for a programmable number of A/D cycles). As a result, at time T1 (924), the offset D/A (FIG. 7, 740) is incremented, generating a −8.0 mV offset 930. The result as depicted in FIG. 9B is that the A/D output 902 takes a −8.0 mV step from 7.5 mV to −0.5 mV. The A/D output 902 is then within the A/D output range (904 and 922) while the input signal 900 goes on to exceed the input range. At time T2 (926), the A/D output 902 again exceeds 7.5 mV (for a programmable number of A/D cycles), which causes the offset D/A (FIG. 7, 740) to increment, generating an additional −8.0 mV step 932 in the D/A output 928, which again offsets the A/D output 902 to −0.5 mV.

Figure 10:
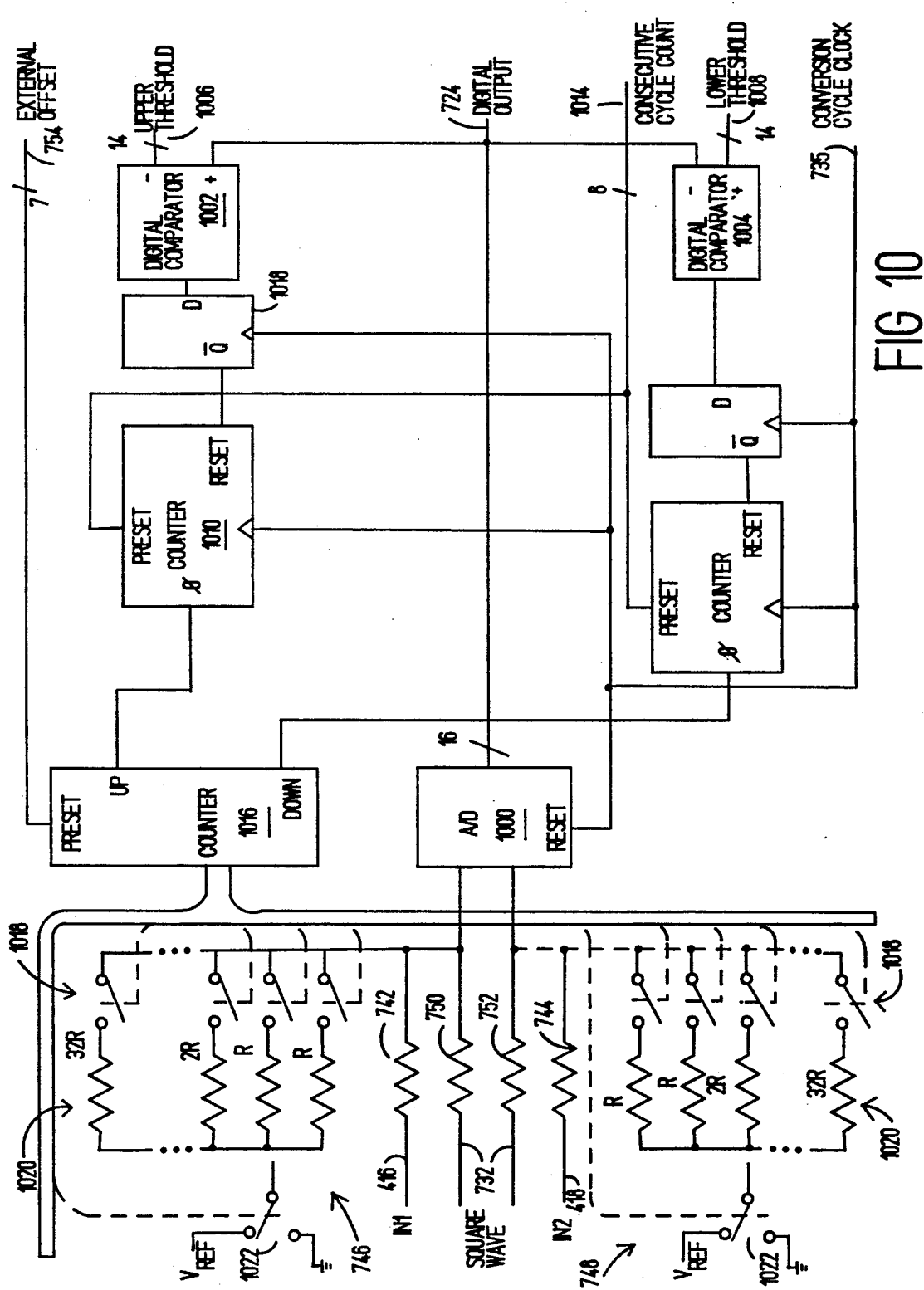
FIG. 10 is a block diagram schematic of the autoranging offset circuitry illustrated in FIG. 7.

FIG. 10 illustrates additional detail for the offset D/A converter depicted in FIG. 7 (FIG. 7, 736 and 740). In FIG. 10, two input signals (416 and 418), complementary square wave signals (732), input resistors (742–752), digital output 724, conversion cycle clock 735 and external offset signal 754 all correspond to the identically numbered elements illustrated in FIG. 7. For simplicity of illustration, elements 704–722, 726–730 and 734 in FIG. 7 are all represented in FIG. 10 by the box labeled A/D (1000).

As illustrated in FIG. 10, the 16-bit A/D digital output 724 (only 14 bits are used) is one digital input on each of two digital comparators (1002 and 1004). The second input on each digital comparator (1002 and 1004) is a 14-bit digital threshold (1006 and 1008) (corresponding to FIG. 9B, 906–920). If the digital output 724 is within the range defined by the upper threshold 1006 and the lower threshold 1008, then the outputs of the digital comparators (1002 and 1004) are at logical "zero". If the digital output 724 is greater than the upper threshold 1006, the output of digital comparator 1002 is at logical "one". Likewise, if the digital output 724 is less than the lower threshold 1008, the output of digital comparator 1004 is at logical "one".

The logic circuitry depicted in FIG. 10 is best understood by following one example path. As discussed in conjunction with FIGS. 7 and 9, the digital output 724 must exceed a digital threshold for a programmable number of consecutive A/D conversion cycles (samples) before an offset D/A is incremented. In FIG. 10, a consecutive samples counter 1010 determines whether the programmable number of consecutive A/D samples has occurred. When the consecutive samples counter 1010 is reset, it is preset to a programmable consecutive cycles count 1014 (maximum is 128 samples, see Appendix 3). The conversion cycle clock 735 (also FIG. 7, 735) occurs once each time the digital output 724 is updated. The consecutive samples counter 1010 is clocked (decremented) by the conversion cycle clock 735. If the consecutive samples counter 1010 reaches zero, an offset counter 1016 is incremented.

If the digital output 724 is within the range defined by the upper threshold 1006 and the lower threshold 1008, the digital comparator 1002 outputs a logical "zero", which in turn clears a flip-flop 1018, which resets the consecutive samples counter 1010. Usually, the consecutive samples counter 1010 is reset by the flip-flop 1018 each A/D conversion cycle and is therefore prevented from reaching zero. However, if the digital output 724 is greater than the upper threshold 1006, the digital comparator 1002 outputs a logical "one" which sets the flip-flop 1018 which permits the consecutive samples counter 1010 to decrement. If the digital output 724 is greater than the upper threshold 1006 for the programmable consecutive cycles count 1014 then the consecutive samples counter 1010 reaches zero and the offset counter 1016 is incremented one count. Symmetrically, if the digital output 724 is less than the lower threshold 1008 for the programmable number of consecutive cycles count 1014 then the offset counter 1016 is decremented one count.

In FIG. 7, resistors 746 and 748 are depicted as single resistors for simplicity of illustration. As illustrated in FIG. 10, the output of the offset counter 1016 actually controls switches 1018 which switch in one or more elements of a weighted resistor network 1020. As also illustrated in FIG. 10, there is a symmetrical arrangement for each of the differential inputs 732. In the preferred embodiment of the present invention, the offset counter 1016 is a 7-bit counter. Six bits control switches 1018 for individual resistors and the most significant (sign) bit controls a supply switch 1022 which controls the supply voltage for the entire array of resistors 1018. Even though switches 1022 switch between a positive voltage and ground, capacitor switching implementation of resistors (section IV below) enables negative offset voltages to be generated.

IV. SWITCHED-CAPACITOR CIRCUITS

In FIGS. 1–10, the block diagrams and schematics illustrate resistors. As will be appreciated by those familiar with CMOS processes, resistor functionality may be physically realized by actual poly resistors, by any of several diffusions, by appropriately biased field effect transistors, or by switched capacitor circuits. For example, in the preferred embodiment of the present invention, the preamp resistor ladders (FIG. 4, 420 and 428) are realized as actual poly resistors. In contrast, resistors 448 and 452 in FIG. 4 are explicitly shown in FIG. 6 as field effect transistors 626 and 630, respectively. In some cases, for clarity of illustration or explanation, the specific realization is not illustrated.

Referring to FIG. 10, resistors 742, 744, 750 and 752 and resistor network 1020 are critical components. For accurate analog to digital conversion, it is essential that these resistors be accurate, stable and precisely matched. In the preferred embodiment of the present invention, these critical resistors are realized by switched capacitor circuits. The use of switched capacitors as a technique to realize precision resistance values in MOS IC design is well known in the MOS IC industry. However, in the preferred embodiment of the present invention, a novel implementation combines a three-phase clock with dead time between phase transitions, voltage doubling, differential circuitry and extensive compensation for residual charges. This is illustrated in FIGS. 11A, 11B and 12.

Figure 11A:
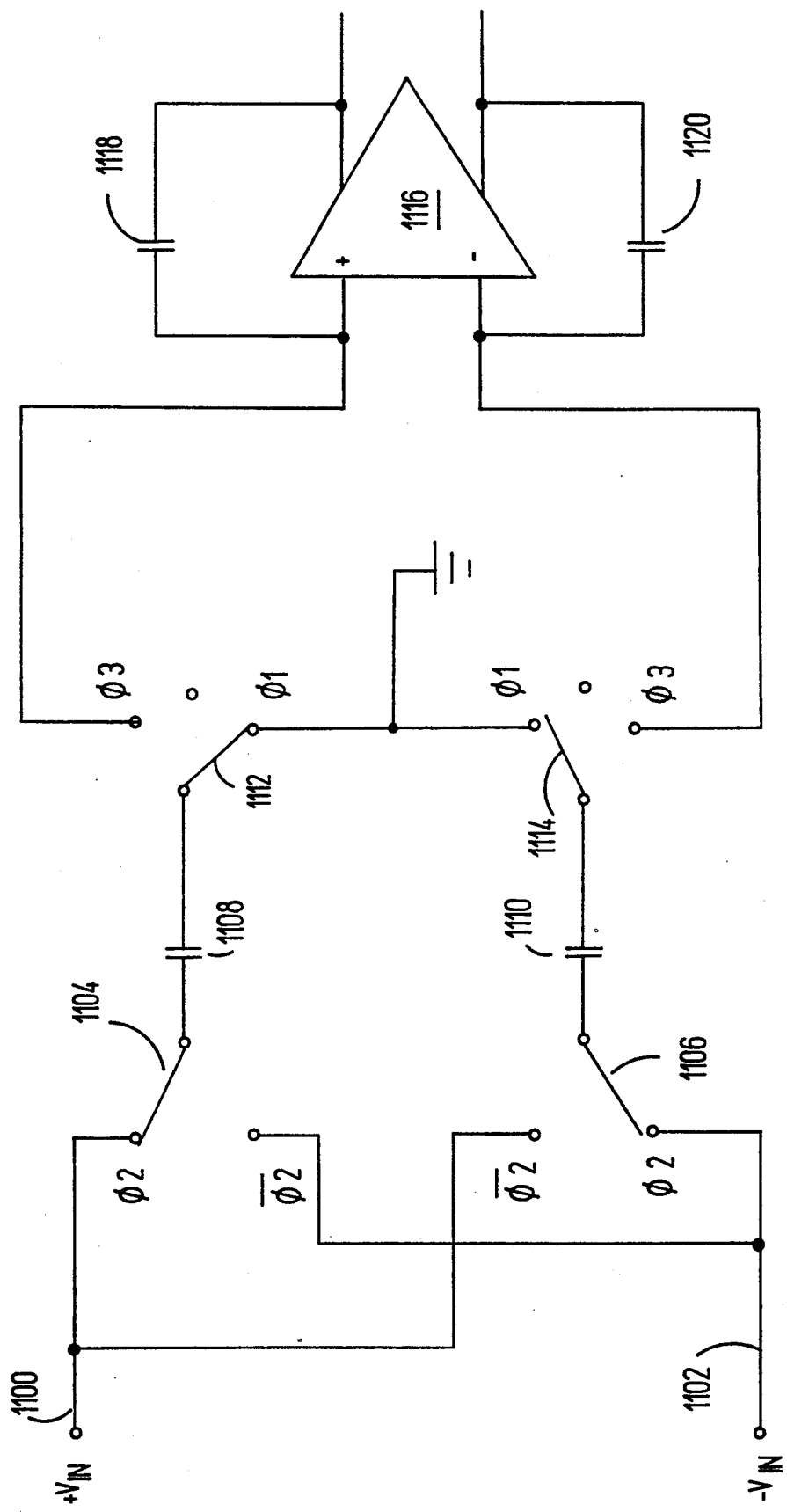
FIG. 11A is a simplified functional schematic of a switched capacitor implementation of a resistor pair.

FIG. 11A illustrates a simplified schematic of a differential switched capacitor circuit as implemented in the preferred embodiment of the A/D conversion portion of the Chip. For example, resistors 742 and 744 in FIG. 7 are implemented as illustrated in FIG. 11A. Complementary input signals (1100 and 1102) pass through two 2-position switches (1104 and 1106), to two switched capacitors (1108 and 1110), through two 3-position switches (1112 and 1114), to a differential integrating amplifier 1116 with integration feedback capacitors (1118 and 1120). In general, the switching capacitors (1108 and 1110) are very small. The switching capacitors (1108 and 1110) are repeatedly charged and each charge is transferred to the integrating capacitors (1118 and 1120). Since the switching capacitors (1108 and 1110) are very small, each charge transfer is very small, so that many charge transfers are required to substantially increase the voltage on the integrating capacitors (1118 and 1120). The slow charging of the integrating capacitors (1118 and 1120) is functionally equivalent to charging the integrating capacitors (1118 and 1120) through large resistors.

Figure 11B:
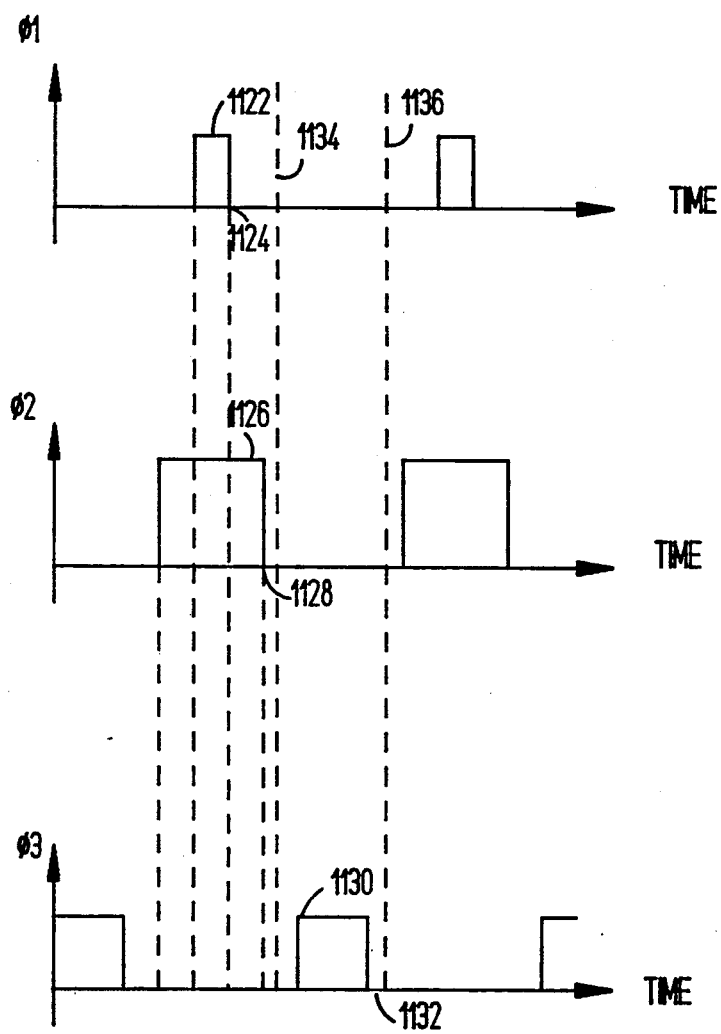
FIG. 11B illustrates a timing diagram for the switched capacitor circuit illustrated in FIG. 11A.

Continuing with FIG. 11, the positions of the switches (1104, 1106, 1112 and 1114) are controlled by a three-phase clock as illustrated in FIG. 11B. Switch contact labels in FIG. 11A correspond to clock phases in FIG. 11B. During phase 1 (1122), the switches (1104, 1106, 1112 and 1114) are in the positions illustrated in FIG. 11A. During phase 1, the first switched capacitor 1108 is charged to the first input voltage 1100 and the second switched capacitor 1110 is charged to the complimentary input voltage 1102. At the falling edge of phase 1 (1124), phase 2 (1126) is still high. At that time, switches 1112 and 1114 switch away from ground to an open position where they are not connected to anything other than the switched capacitors (1108 and 1110). This open position prevents any charge leakage before the following switch transition and permits some residual charge compensation as explained below.

At the falling edge of phase 2 (1128), switches 1104 and 1106 toggle to the opposite position. For simplicity, assume that the input voltages 1100 and 1102 are equal magnitude but opposite polarity. At the falling edge of phase 2 (1128), the side of switched capacitor 1108 attached to switch 1104 is switched to the complementary input voltage 1102. The other side of switched capacitor 1108, which is floating free, remains $-V_{in}$ Volts (1100) relative to the side which just switched, or $-2*V_{in}$ Volts relative to ground.

At the rising edge of phase 3 (1130), switches 1112 and 1114 switch to the inputs of the amplifier 1116. The amplifier 1116 drives the amplifier inputs to virtual ground, which for each switched capacitor (1108 and 1110) is a voltage change of $2*V_{in}$ Volts, thereby transferring twice the charge of each switched capacitor (1108 and 1110) to the integrating capacitors (1118 and 1120). At the falling edge of phase 3 (1132), switches 1112 and 1114 again switch away from the amplifier inputs to a neutral position, preventing any charge leakage to the amplifier 1116 during following switch transitions.

Note that at time 1134 there is a dead time between the falling edge of phase 2 (1128) and the rising edge of phase 3 (1130). Likewise, at time 1136 there is a dead time between the falling edge of phase 3 (1132) and the rising edge of phase 2. Likewise, there are delays between any phase transition and the next transition of any phase. As will be seen below, these delays between transitions facilitate charge compensation for MOS switches.

In the preferred embodiment of the present invention, the switching frequency is 4.096 MHz and the smallest switching capacitors (1108 and 1110) are 40 femtofarads. Non-ideal switching characteristics of MOS transistors, which can be ignored in some applications, become very important at this relatively high frequency with such small capacitances. For example, in a MOS transistor, there is some capacitance between the gate and the source/drain channel. In addition, when a MOS transistor turns off, some residual charge remains in the source/drain channel.

In the preferred embodiment of the present invention, four design features have been implemented to minimize the effects of residual channel charge as follows:
1. Differential circuitry to reduce common mode effects;
2. Dead time between clock phases transitions to provide a dead time for residual charge compensation;
3. Use of NMOS/PMOS pairs so that two equal but opposite charges cancel; and
4. Use of dummy transistors which switch in opposite directions so that equal and opposite charges cancel.

Figure 12A:
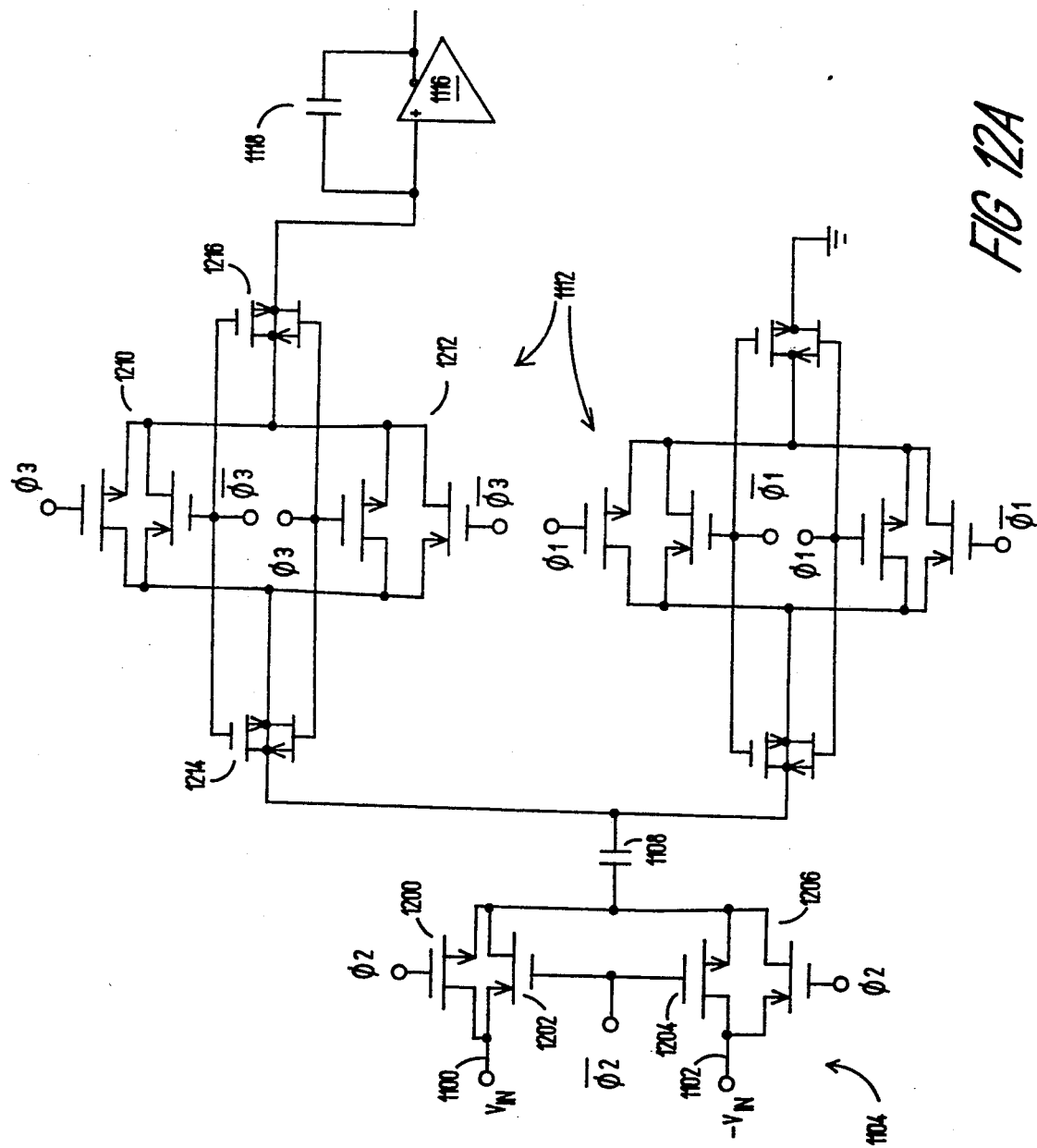
FIG. 12A is a detailed schematic of half of the switched capacitor circuit illustrated in FIG. 11A.

FIG. 12A illustrates additional schematic detail for switches 1104 and 1112 which were functionally described above in conjunction with FIG. 11A. In FIG. 12A, two complementary input voltaqes (1100 and 1102), a switched capacitor 1108 and an integrating amplifier 1116 with integrating capacitor 1118 are all identical to the corresponding numbered elements in FIG. 11A. In addition, the three phase clock designations correspond to the designations illustrated in FIG. 11B.

Continuing with FIG. 12A, NMOS transistor 1200, PMOS transistor 1202, NMOS transistor 1204, and PMOS transistor 1206 all combined correspond to FIG. 11A, switch 1104. When phase 2 is high (FIG. 11A, 1126), transistors 1200 and 1202 are on, connecting the switched capacitor 1108 to the first input voltage 1100. The use of NMOS/PMOS pairs compensate for residual channel charge. When the gate signal switches, positive or negative charge will be injected into the source/drain channel. NMOS/PMOS pairs of identically sized transistors are used so that two equal but opposite injection charges will cancel.

Continuing With FIG. 12A, switch 1112 in FIG. 11A is realized by an overall group of 16 transistors. When phase 3 is high (FIG. 11B, 1130), two switching NMOS/PMOS pairs (1210 and 1212) are all on. Two dummy NMOS/PMOS pairs are off (1214 and 1216) but their sources are shorted to their drains, providing a conducting path. When phase 3 goes low (FIG. 11B, 1132), the switching pairs (1210 and 1212) all turn off. When the switching pairs turn off, half the residual charge of each transistor leaves via the source and half via the drain. Again, having NMOS/PMOS pairs tends to cancel charges. Finally, any remaining residual charges will tend to be canceled by the opposite switching dummy pairs (1214 and 1216).

NMOS/PMOS pairs 1210 and 1212 are fabricated from four identically sized transistors. Dummy pairs 1214 and 1216 are half the size of pairs 1210 and 1212 since the role of the dummy pairs is to cancel half the total channel charge.

Due to process limitations, charge cancellation is still not perfect and additional improvement is gained by providing dead times between clock transitions as illustrated in FIG. 11B (for example, 1134 and 1136). These dead times provide time for charge movements to substantially stabilize between clock phase changes.

Figure 12B:
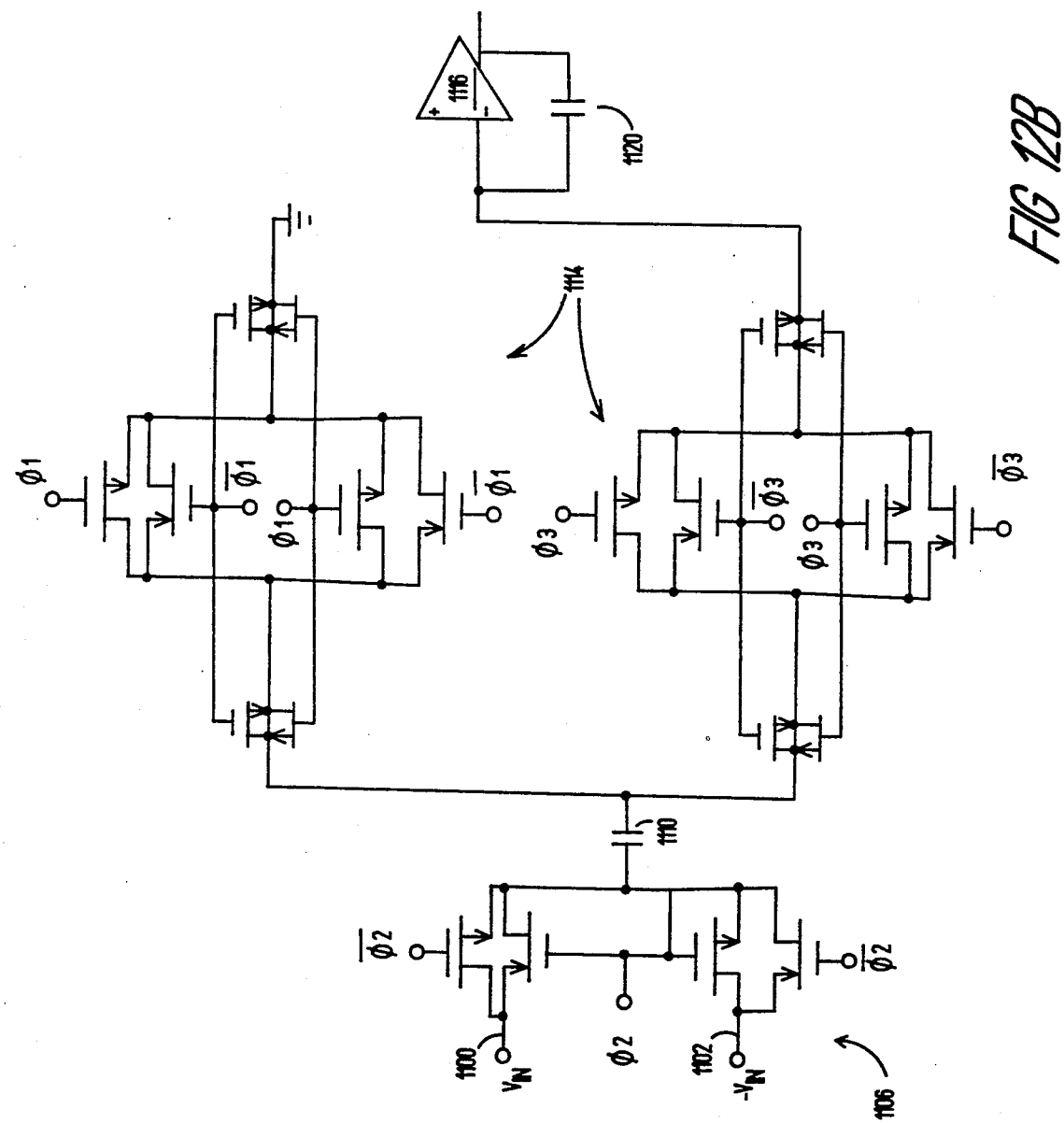
FIG. 12B is detailed schematic of half of the switched capacitor circuit illustrated in FIG. 11A.

FIG. 12B illustrates additional detail for switches 1106 and 1114 which were functionally described in conjunction with FIG. 11A. The circuitry illustrated in FIG. 12B is functionally identical to equivalent circuitry illustrated in FIG. 12A.

V. ANALOG AVERAGING AND ANALOG OUTPUT DRIVER

Figure 13:
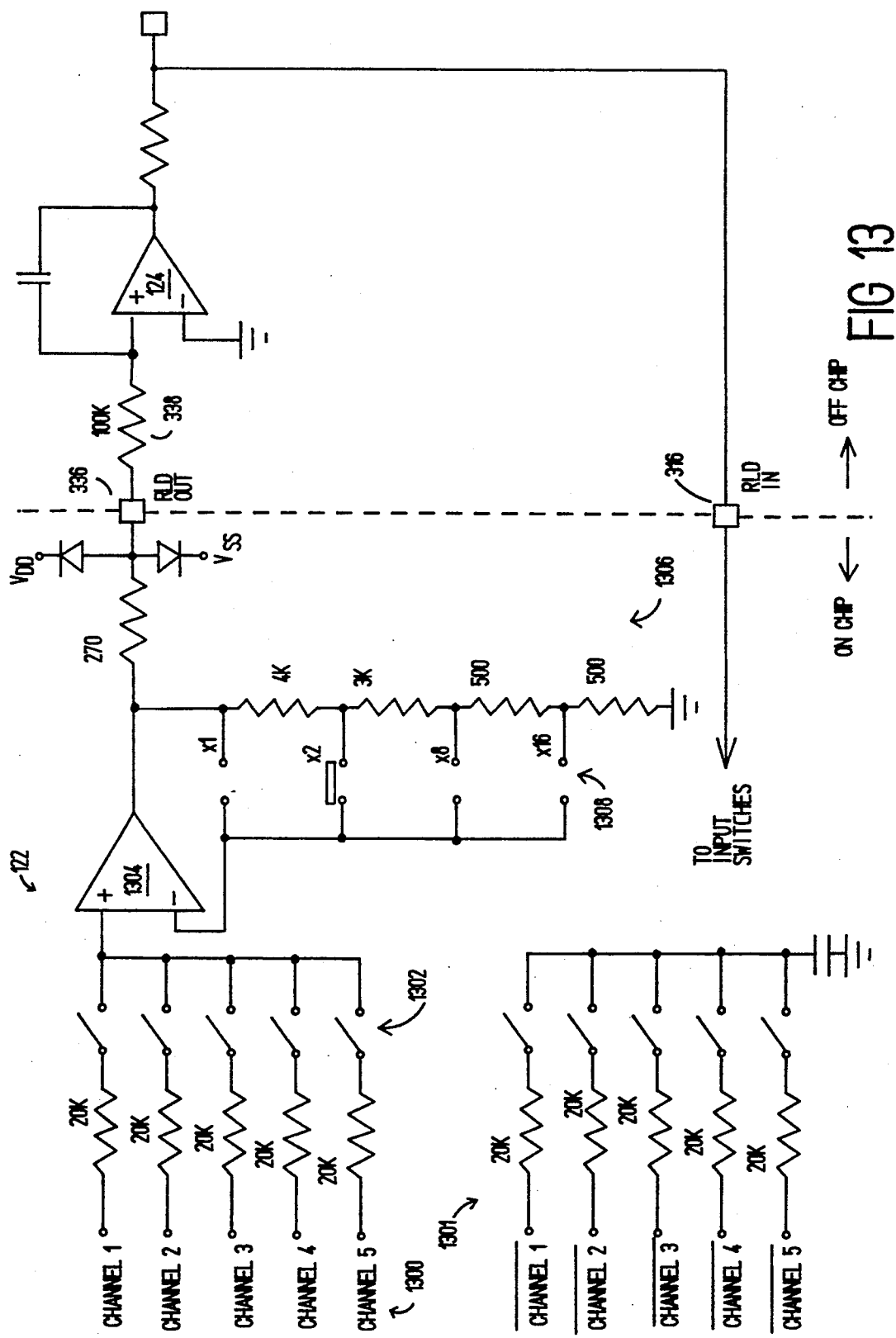
FIG. 13 is a simplified functional schematic of the right-leg-drive circuitry illustrated in FIG. 3.

FIG. 13 illustrates additional detail for the right leg drive averaging circuit (FIGS. 1,2 and 3, 122). FIG. 13 is divided by a dashed line. Circuitry to the left of the dashed line is internal to the Chip. Circuitry to the right of the dashed line is external, as illustrated in FIG. 3.

As illustrated in FIG. 13, there are five summing signal inputs 1300. Each summing signal input 1300 is an output of an analog preamp (FIG. 4, 416). Each summing signal input is individually switched (1302) to a first input of a summing amplifier 1304. Complementary preamp outputs (FIG. 4, 418) are connected to an identical switch arrangement 1301 with a capacitive load to provide symmetrical loading of preamp outputs. The input switches (1302) are individually controlled by digital control circuitry (discussed below in section IX). The summing amplifier 1304 has a variable gain feedback path comprising a resistor ladder 1306 and gain switches 1308. The resistor ladder 1306 and gain switches 1308 provide an averaging amplifier 1302 closed loop gain of 1, 2, 8 or 16. For example, the closed loop gain is 2 for the switch position illustrated in FIG. 13. Note that the feedback path is such that the averaging amplifier (1304) gain is independent of the number of channels being summed.

Recall from FIG. 4 that the analog preamps have a programmable gain of 2, 4, 16 or 32. Continuing with FIG. 13, the averaging amplifier (1304) gain is dependent on the preamp gain (FIG. 4) so that the combined gain of preamp and averaging is fixed at 32. For example, if preamp gain is 16 (as depicted in FIG. 4), then the averaging amplifier (1304) gain is set at 2 (as depicted in FIG. 13) for an overall gain of 16*2=32.

The averaging amplifier 1304 is a two stage chopper stabilized amplifier similar in design to the preamps as illustrated in FIGS. 5 and 6 and the A/D integrating amplifier illustrated in FIG. 8. As illustrated in FIG. 13 (and FIGS. 1, 2 and 3), the summed signal is amplified by an external integrator 124 and the resulting signal is routed back onto the Chip (316) for optional switching to one of the lead connections (discussed further below in conjunction with FIG. 14).

VI. INPUT SWITCHES AND LEADS-OFF DETECTION

Figure 14:
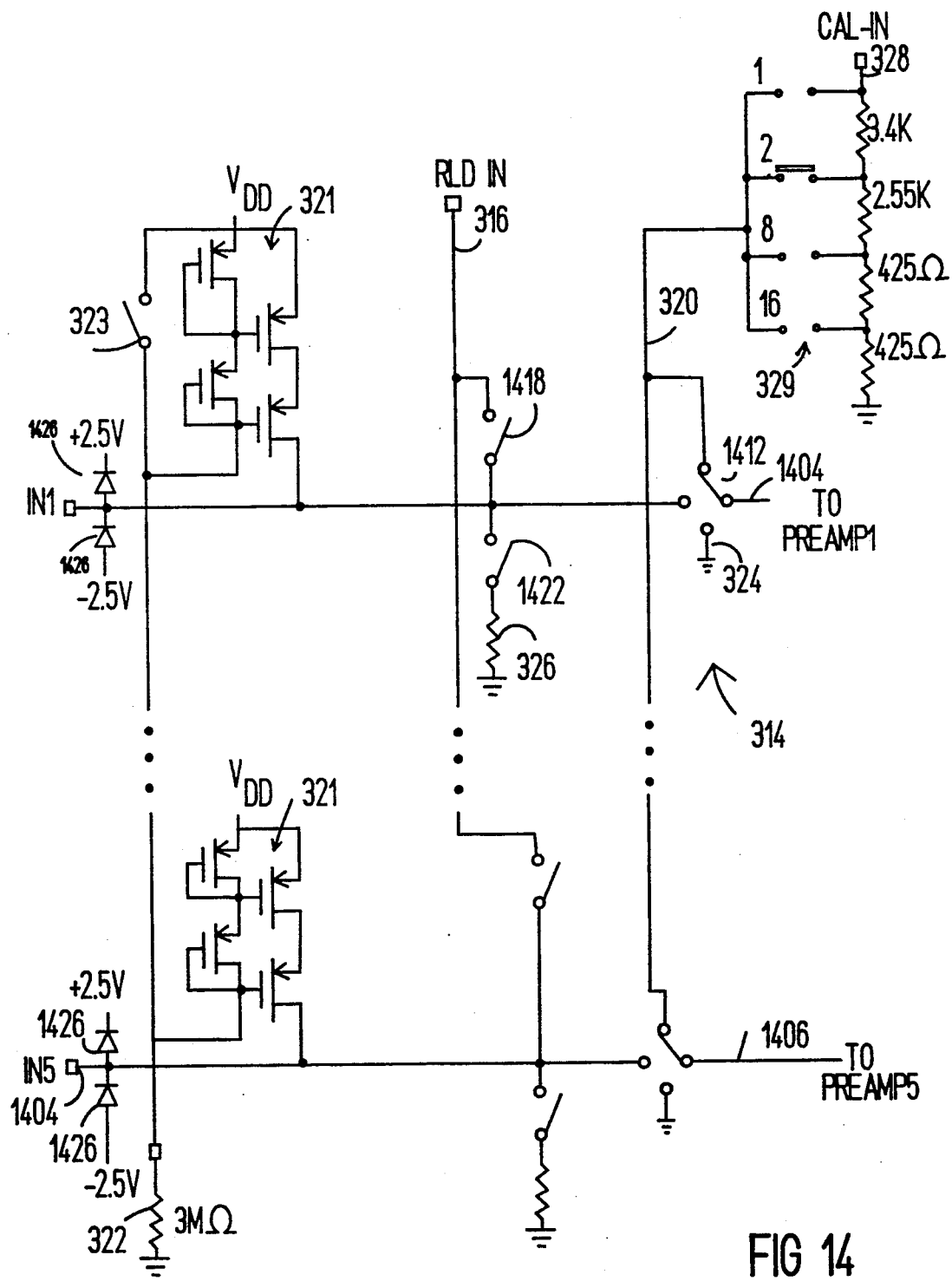
FIG. 14 is a simplified functional schematic illustrating additional detail for input lead switching, diode protection, and the leads-off current sources illustrated in FIG. 3.

FIG. 14 is a simplified functional schematic illustrating additional detail of input switching (FIG. 3, 314), diode protection of inputs, and the DC leads-off current sources (FIG. 3, 321). FIG. 14 illustrates 2 of the 5 channels. Each channel is substantially identical for the functions illustrated.

In FIG. 14, using channel 1 as an example, switch 1412 can switch the input of the first preamp (1404) (FIG. 4A, 400) to an attenuated calibration voltage 1414, to ground 324, or to the first signal lead 1402. Switch 1418 can switch the first signal lead 1402 to the output of an external right-leg-drive amplifier 316, thereby making the first signal lead an output signal. Switch 1422 can switch the first signal lead 1402 to a resistor 326 to ground.

FIG. 14 also illustrates diode protection of input circuitry. Input protection diodes 1426 are connected to power supply circuitry (not illustrated) which is isolated from the main analog $V_{dd}$ and $V_{ss}$ supplies. The protection diodes 1426, in conjunction with the external 33 KOhm resistors (FIG. 3, 306), have sufficient current capability to handle peak currents of 150 milliamps for the several milliseconds of defibrillator pulse duration.

Continuing with FIG. 14, an attenuator 329 (also FIG. 3, 329) attenuates an external calibration signal (328) by a factor of 1, 2, 8 or 16. The attenuation factor is automatically set to half the preamp gain (FIG. 4, 422), except when in a marker pulse mode described below. For example, if the preamp gain is 16 (as depicted in FIG. 4), the calibration attenuation is automatically set to 8, as depicted in FIG. 14.

A common convenience feature in an ECG application is a 1 mV marker pulse. In the present invention, this is realized by switching the input switch 1412 to the preamp calibration signal 320 and switching the attenuator 329 for maximum attenuation (1/16). The pulse is then provided by the calibration D/A (FIG. 3, 332).

Also illustrated in FIG. 14 are the leads-off current sources 321 (also FIG. 3, 321). Each input signal line (1402, 1404) is connected directly to a current source 321. Each of the five leads-off current sources mirrors a current which is determined by a single external resistor 322 (also FIG. 3, 322). In an ECG application, the magnitude of the current is typically in the range of 5 to 20 nanoamps. A single leads-off switch 323 (also FIG. 3, 323) turns off all five leads-off current sources 321 by shorting transistor drains to sources, eliminating current flow through the transistor circuits.

Leads-off detection is accomplished by opening the leads-off switch 323 allowing current to flow out each signal lead (1402, 1404), through each electrode, through the patient, and back through the right leg drive output (see FIGS. 1 and 2). The right leg drive circuit (FIGS. 1, 2, 3 and 13, 124) actively drives the average voltage at the patient to virtual ground. Resulting DC voltages at the signal leads (1402, 1404) are measured by the signal preamps and A/D converters as discussed above (FIGS. 4A and 7). If a lead is inadequately attached or if a lead falls completely off, the path to virtual ground is interrupted and the corresponding preamp input floats toward $V_{DD}$, saturating the preamp.

In some applications, the external signals may be AC coupled to the Chip. For example, in fetal monitoring, even the relatively small currents involved in leads off detection are avoided. If the external signals are AC coupled, the DC leads-off method described above will not work.

For AC coupled applications, after initial connection or after a lead falls off, an external series coupling capacitor may have substantial residual charge. It is common in electrocardiographs to provide a user controllable switch from an input signal lead to a resistor to ground to discharge the series signal capacitor. The resistor is called an "insto" resistor. As illustrated in FIG. 14, switch 1422 and resistor 326 (also FIG. 3, 326) provide "insto" capability for the Chip.

VII. IMPEDANCE MEASUREMENT

FIG. 15 is a block diagram illustrating additional detail for the AC impedance measurement circuitry (FIGS. 1, 2 and 3, 120). As illustrated in FIG. 3 and in FIG. 15, A/D switches 362 can switch the input of the A/D converter 346 in the fifth channel from an analog preamp output signal (354) to an impedance signal (356).

Continuing with FIG. 15, the impedance signal is generated by four current sources (1502, 1504, 1506 and 1508). Current from a first pair of current sources (1502, 1504) is chopped by a first chopper 1510, alternately flowing through patient leads, and then through a second pair of current sources (1506, 1508). This is explained further in the discussion of FIG. 16 below. The magnitude of the second pair of current sources (1506, 1508) is determined by an external resistor 360 (also FIG. 3, 360), an amplifier 1514 and current source 1505. A separate amplifier 1512 forces the magnitude of the first pair of current sources (1502, 1504) to be identical to the magnitude of the second pair of current sources (1506, 1508). The voltages resulting from the chopped current sources are synchronously rectified by a second chopper (1515), thereby providing an unamplified DC signal to the input of the A/D 346.

Continuing with FIG. 15, calibration switches 1516 can switch the common current source outputs and the input of the second chopper 1515 to precision calibration resistors 1518. The precision calibration resistors 1518 are implemented using switched capacitor circuits as illustrated in FIGS. 12A and 12B. Both choppers (1510 and 1515) can also be stopped in a straight through state which removes the current sources (1502, 1504, 1506 and 1508) from the signal path, thereby providing a nonchopped, nonmodified, nonamplified path straight from external pads to the input of the A/D 346.

Continuing with FIG. 15, switches 1520 can open the signal leads, removing the impedance circuitry from the external signal leads for calibration or other purposes. Also, the inputs to the A/D converter 346 can be grounded by grounding switches 1522 for calibration of the A/D converter 346. When the grounding switches 1522 are closed, input switches 1520 also disconnect the input leads and the choppers (1510 and 1515) are switched to the straight through state described above which also removes the current sources from the signal path.

FIGS. 16A and 16B are simplified functional schematics illustrating the external effect of the first current chopper (FIG. 15, 1510) in the impedance measurement circuitry. FIGS. 16A and 16B are "inside-out" in that the Chip 100 is the circuitry outside the dashed line rectangle and the external world is inside the dashed rectangle. As illustrated in FIG. 16A, the first current chopper is functionally equivalent to eight switches (1610, 1612, 1613, 1614, 1616, 1618, 1619 and 1620). The eight switches are controlled by a four phase clock signal (not illustrated). The state of the eight switches alternates between a first state illustrated by FIG. 16A and a second state illustrated by FIG. 16B.

In the first state (FIG. 16A), current flows from current source 1604, through switch 1614, through the patient 1600, through switch 1620, and through current source 1608. Current from current source 1602 bypasses the patient 1600, flowing through switches 1612 and 1618 and through current source 1606.

In the second state (FIG. 16B), current flows from current source 1602, through switch 1610, through the patient 1600 in a direction opposite to the direction in the first state (FIG. 16A), through switch 1616 and through current source 1606. Current from current source 1604 bypasses the patient 1600, flowing through switches 1613 and 1619 and through current source 1608.

In the straight through state (not illustrated), switches 1610, 1614, 1616 and 1620 are open and switches 1612, 1613, 1618 and 1619 are closed. Therefore, in the straight through state, all currents remain within the Chip and current through all current sources (1602, 1604, 1606, 1608) is disconnected from the signal paths.

AC impedance measurement (which is at a relatively high frequency) and low frequency signal measurement can occur simultaneously. This may be seen by examining the effect of external passive components (304, 306, 308 and 312) as illustrated in FIGS. 16A and 16B (and FIG. 3). For example, in FIGS. 16A and 16B, external resistors 306 and external capacitors 308 provide low pass filtering for voltage signal leads (1642 and 1644). The chopping frequency for the impedance measurement choppers is either 32 KHz or 64 KHz. At either frequency, the impedance of the patient 1600 is on the order of 100 Ohms. Therefore, components 306 and 308 in the voltage signal leads (1642 and 1644) present an impedance which is several orders of magnitude greater than the AC impedance path through the patient. Therefore, the low frequency voltage signal path (1642 and 1644) does not interfere with the high frequency signal path (1646 and 1648).

Also note in FIGS. 16A and 16B that the low pass filtering (306 and 308) in the low frequency signal path (1642 and 1644) greatly attenuates (20 dB at 40 Khz) the relatively high frequency AC impedance signal. In addition, the A/D conversion circuitry (FIG. 7) rejects 32 KHz and 64 KHz signals. Therefore, AC impedance signals do not interfere with low frequency voltage signal measurements.

FIG. 17 illustrates additional detail for the impedance measurement current sources (FIG. 15, 1502, 1504, 1505, 1506 and 1508) and associated controlling amplifiers (FIG. 15, 1512 and 1514). In FIG. 17, transistors 1702, 1704, 1706 and 1708 correspond to FIG. 16, current sources 1602, 1604, 1606 and 1608 respectively. Likewise, in FIG. 17, transistors 1702, 1704, 1705, 1706 and 1708 correspond to FIG. 15, current sources 1502, 1504, 1505, 1506 and 1508 respectively. Transistors 1710, 1712, 1713, 1714, 1716, 1718, 1719 and 1720 correspond to switches 1610, 1612, 1613, 1614, 1616, 1618, 1619 and 1620 respectively in FIGS. 16A and 16B.

Continuing with FIG. 17, external resistor 360 (also FIGS. 3 and 15, 360) controls the magnitude of the second pair of current sources (1708, 1706) via a chopper stabilized amplifier 1514 (also, FIG. 15, 1514). The range of current for current sources 1706 and 1708 in the preferred embodiment is between 90 microamps and 180 microamps. A second chopper stabilized amplifier 1512 (also FIG. 15, 1512) monitors a voltage 1726 which is in the patient bypass path, and controls the magnitude of the first pair of current sources (1702, 1704). For simplicity of illustration, bias circuitry and common mode feedback circuitry are not illustrated.

VIII. SERIAL CHAINING OF MULTIPLE CHIPS

Figure 18:
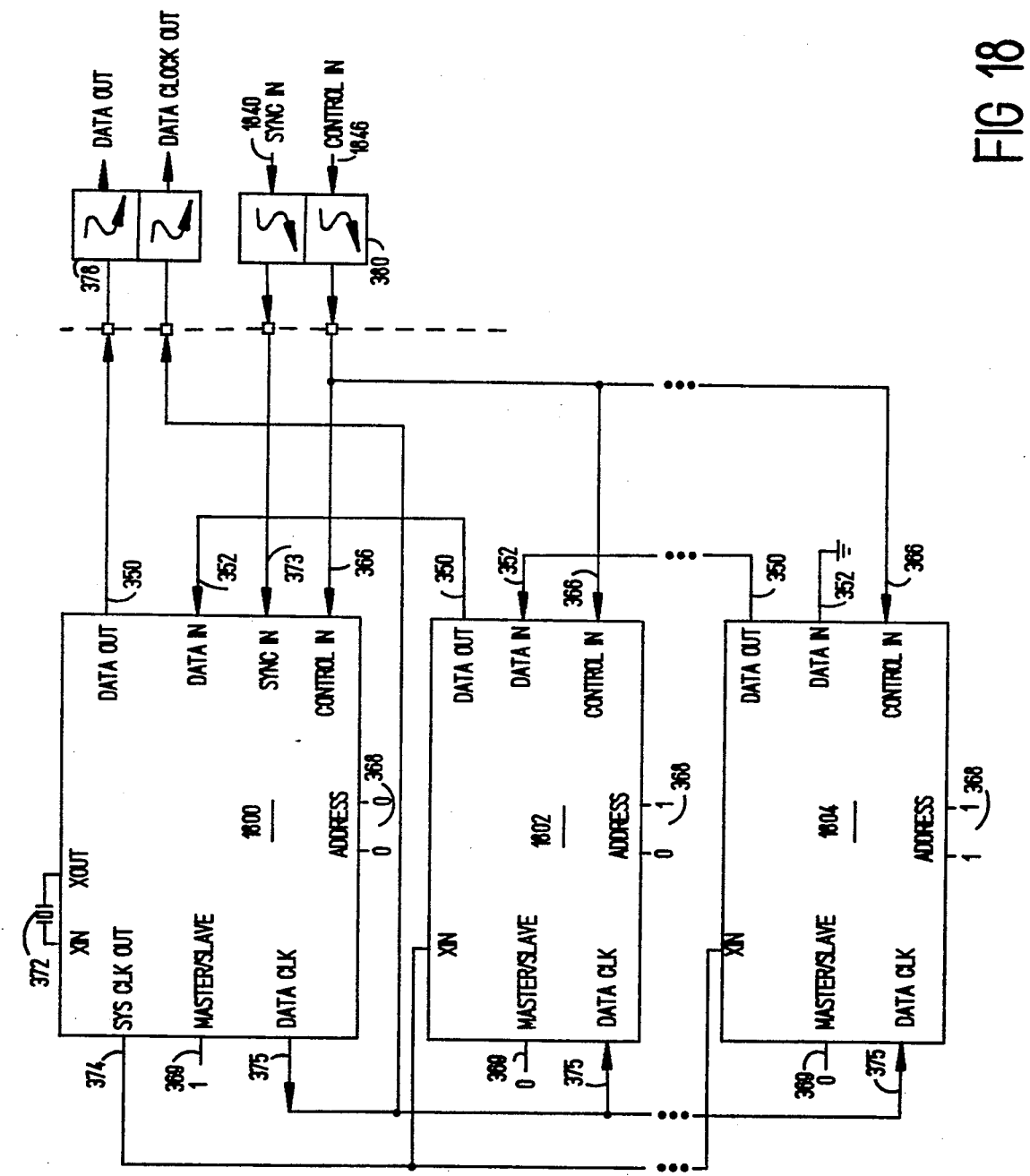
FIG. 18 is a block diagram illustrating serial interconnection of multiple Chips.

FIG. 18 is a simplified block diagram illustrating serial interconnection (serial chaining) of Chips. In FIG. 18, 3 IC's (1800, 1802 and 1804) are depicted. However, any number of Chips up to 6 may be serially connected. A first Chip 1800 has a master/slave pin 369 (also FIG. 3, 369) tied to logical 1, making the first Chip 1800 the master chip. Accordingly, Chips 1802 and 1804 have master/slave pins (369) tied to logical 0, making them slave chips. Master Chip 1800 as illustrated uses an external crystal 372 (also FIG. 3, 372). Master Chip 1800 then provides a system clock signal 374 (also FIG. 3, 374) and a data clock signal 375 (also FIG. 3, 375) to each slave Chip (1802 and 1804). Each Chip has a two bit address 368 (also, FIG. 3, 368). With two bits, there can only be four unique addresses. If there are more than four chips, some chips will share addresses.

The first Chip in the serial chain (slave Chip 1804 in FIG. 18) has a serial data input port 352 which is grounded. Slave Chip 1804 has a serial data output port 350 (also FIG. 3, 350) which is connected to a serial data input port 352 of slave Chip 1802. Likewise, slave Chip 1802 has a serial data output port 350 connected to a serial data input port 352 of master Chip 1800. Master Chip 1800 has a serial data output port 350 which is connected to an external optical coupler 378. As data is clocked out on each serial data output port 350, data is simultaneously being clocked in on each serial data input port 352, all synchronized by the master data clock 375. Data clock 375 is also connected to an external optical coupler 378 for use by the external system receiving the serial output data 350 for master chip 1800.

As also illustrated in FIG. 18, an external synchronization signal 1840 is received by master chip 1800 (signal 1844) (FIG. 3, 373) via an external optical coupler 1842. The external synchronization signal 1840 is used to synchronize the conversion cycle internal to a Chip with external events.

An external serial input control signal 1846 is received via an external optical coupler 380 (also FIG. 3, 380) and simultaneously received by each Chip (1800, 1802 and 1804) as a control input signal 366 (also FIG. 3, 366). Additional detail for this signal is provided in section IX below.

For each sample period, each Chip (1800, 1802 and 1804) potentially generates five 16-bit words of data (80 bits total). With the maximum of 6 IC's, the maximum total output data per sample period is 480 bits. Individual channels may be turned off or individual channels may be used for analog output (right-leg-drive), reducing the total bits per sample period.

IX. DIGITAL CONTROL

Throughout the discussion above of overall function, preamps, A/D conversion, offset, etc., it was pointed out that various functions are under programmable control. For example, the following functions are controllable by the digital control circuitry:

1. Command parsing (address, channel, function)
2. Input switch circuitry (FIG. 14, 1412, 1418 and 1422)
3. Calibration attenuator (FIGS. 3 and 14, 329)
4. Preamp gain (FIG. 4, 422)
5. Offset D/A preset (FIGS. 7 and 10, 754)
6. Offset D/A threshold (FIG. 10, 1006 and 1008)
7. Offset D/A delay (FIG. 10, 1014)
8. Calibration D/A (FIG. 3, 332)
9. A/D converter resolution and rate (FIG. 7, 728 and 734)
10. A/D conversion mode (FIG. 7, 732)
11. Impedance current source frequency (FIG. 15, 1728)
12. Impedance A/D switches (FIGS. 3 and 15, 362)
13. Output data controller (FIG. 3, 348)
14. Output data clock (FIG. 3, 375)
15. Power down of unused channels (FIG. 5, 550 and 552)
16. Averaging circuitry (FIG. 13)
17. Testing modes One serial input control signal (FIGS. 3 and 18, 366) is simultaneously received by each Chip. Input control signals are three byte (24 bits) commands which contain both address and data information. The first byte of a command (address) determines how the last 2 bytes (data) are interpreted and which circuitry is affected (see appendix 1). There are 3 types of input commands, established by the first byte, as follows:

1. The input data is interpreted as control data. There are 3 types of input control data as follows:
    A. Channel control data for a specific channel address at a specific Chip address (see appendix 2).
    B. Chip control data for a specific Chip address (see appendix 3).
    C. System control data which is the same for all Chips (see appendix 4).
2. The input data is interpreted as D/A data. There are 2 types as follows:
    A. Offset D/A data for a specific channel address at a specific Chip address.
    B. Calibration D/A data for a specific Chip address.
3. The input data is ignored and the command is interpreted to modify the next serial output data. There are 3 types of output control as follows:
    A. For each chip and each channel, output channel control bits (output counterpart to appendix 2).
    B. For each chip and each channel, output offset D/A values.
    C. For each chip, output chip control bits, system control bits, calibration D/A value, and the contents of a status register.

Figure 19:
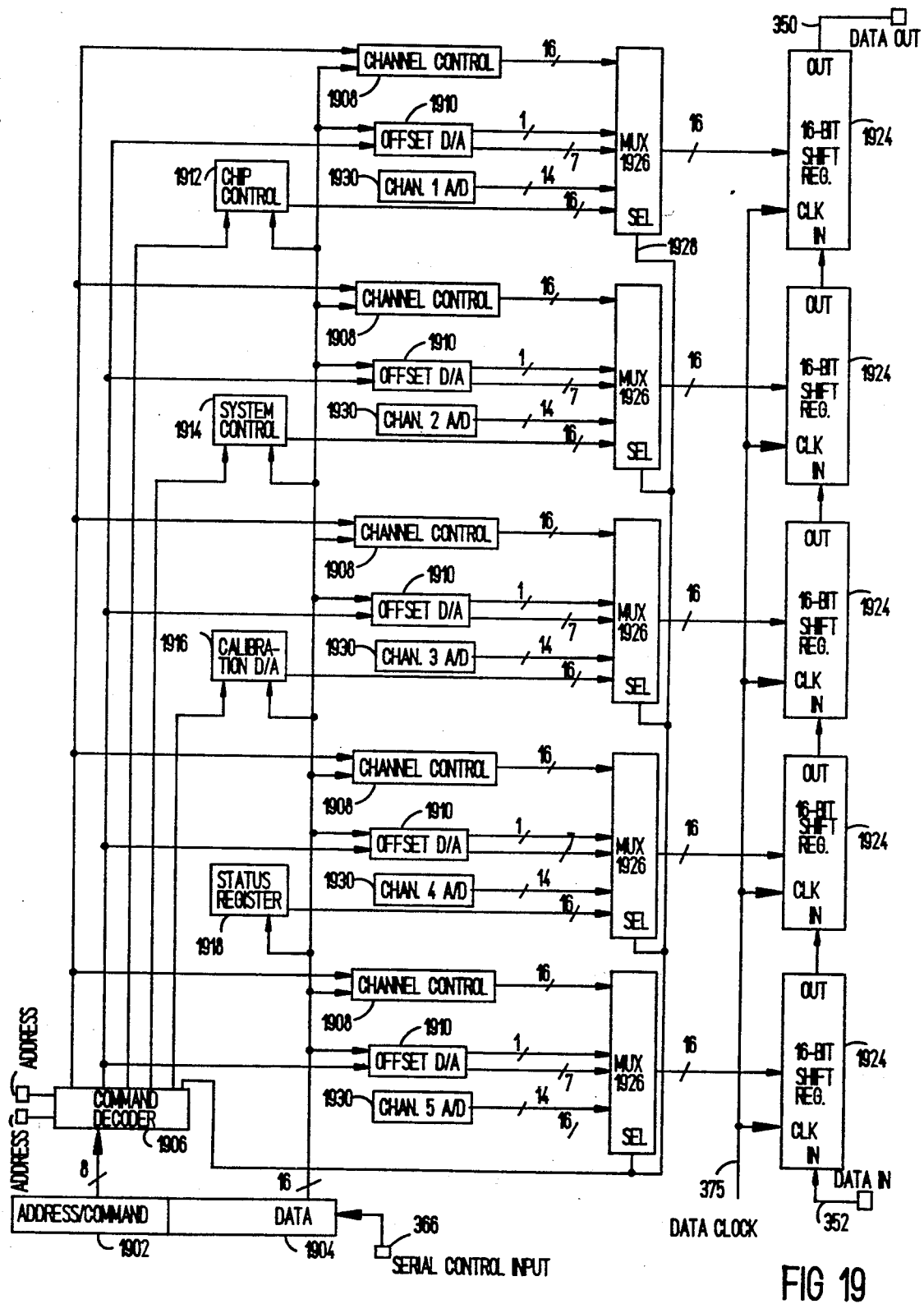
FIG. 19 is a block diagram illustrating additional detail for digital input and output control functions illustrated in FIG. 3.

FIG. 19 illustrates a block diagram overview of the serial input command circuitry (illustrated in FIG. 3 as digital control 364) and the serial output circuitry (illustrated in FIG. 3 as digital output controller 348). Digital control 364 in FIG. 3 comprises boxes 1902–1918 and 1930 in FIG. 19. Digital output control 348 in FIG. 3 comprises boxes 1924 and 1926 in FIG. 19.

As illustrated in FIG. 19, a serial control input 366 (also FIG. 3, 366), is comprised of 8 bits of address/command 1902 and 16 bits of data 1904. The 8 bits of address/command are decoded by a command decoder 1906. The 16 bits of input control data 1904 may be used to update channel control registers 1908, offset D/A's 1910, a chip control register 1912, a system control register 1914, or a calibration register 1916, depending on the output of the command decoder 1906.

Also illustrated in FIG. 19 is a DATA IN signal 352 (also FIGS. 3 and 18, 352), a DATA OUT signal 350 (also FIGS. 3 and 18, 350) and five 16-bit shift registers 1924. Each 16-bit shift register 1924 will receive 16 bits of parallel data selected from up to five parallel inputs to a digital multiplexer 1926. Each multiplexer 1926 has an input select signal 1928 which is driven by the command decoder 1906. The command decoder 1906 determines whether the output data 1922 is A/D data or other status or control data. Normally, a shift register 1924 is loaded with 14 bits of data from an A/D converter 1930, one bit of increment/decrement data from a corresponding offset D/A 1910 and one parity bit. The direction of change associated with the single bit of offset data may be inferred from previous A/D outputs. Alternatively, a serial input command 1902 can direct the command decoder 1906 to direct each multiplexer 1926 to select 7 bits of offset D/A data (1910) instead of A/D data (1930). Another alternative output selection causes the contents of the channel control registers 1908 to be selected for data output 1922. Still another alternative selection causes the chip control register 1912 to be output instead of channel 1 A/D data, the system control register 1914 to be output instead of channel 2 A/D data, the calibration D/A register 1916 to be output instead of channel 3 A/D data and a status register 1918 to be output instead of channel 4 and channel 5 A/D data.

Appendices 1-4 provide additional detail for serial control input address/commands and data. Appendix 1 details the function of the first byte (address/command). Appendix 2 details the function of the second two bytes when interpreted as channel control bits. Appendix 3 details the function of the second two bytes when interpreted as chip control bits. Appendix 4 details the function of the second two bytes when interpreted as system control bits. For serial command input, the most significant bit is received first.

As detailed in appendix 1, the first byte of a command contains a 3-bit Chip address and a 3-bit channel address. Valid channel addresses are restricted to 1-5 and 7 (all channels). Channel addresses of 0 or 6 are used to designate other control functions as detailed in appendix 1. Likewise, valid chip addresses are restricted to 1-4 and 7 (all chips). Chip addresses of 5 or 6 are used to designate other control functions as detailed in appendix 1.

As detailed in appendix 2, channel control bits control the channel input signal switches (see FIG. 14, 1412 and 1422), whether the buffered right leg drive signal is switched back into the Chip or remains external (see FIG. 14, 1418), whether the offset D/A is exclusively externally controlled or is in a combined autoranging-/external control mode (see FIG. 10, 1024) and individual channel power (see FIG. 5, 550, 552).

As detailed in appendix 3, chip control bits set preamp gain control switches (see FIG. 4, 422), set the consecutive cycle count register for the offset D/A's (see FIG. 10, 1014), set offset D/A threshold values (see FIG. 10, 1006 and 1008), the switch which controls the leads-off current sources (see FIG. 14, 1412), the input calibration attenuator (see FIG. 14, 329) and the A/D converter mode (see FIG. 7, 730). As also detailed in appendix 3, three chip control bits are used to configure the fifth channel impedance measurement circuitry. One exception is the combination 001 which puts the Chip into a special production test mode.

As detailed in appendix 4, system control bits set a counter/divider value (FIG. 7, 734) which determines the A/D conversion rate and resolution tradeoff, the data clock frequency, the number of data words to be clocked out during each sample period and various chopper clock states. The external microprocessor must ensure that the number of 16-bit words serially shifted out during each sample period is consistent with the number of enabled channels. FIGS. 4B and 4C illustrate chopper states. A two-phase chopper clock (CHOP1 and CHOP2) which controls the chopper states is not explicitly illustrated. If the chopper clock is off, one of four possible states of the two-phase signal is set as detailed in appendix 4.

The foregoing description of the present invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

APPENDIX 1
MOST SIGNIFICANT BYTE OF 3 BYTE COMMAND

| D/A Bit | Channel Address | Chip Address | Command/Data Function |
|---|---|---|---|
| | | | INPUT CONTROL BITS |
| 0 | NOT 0 NOT 6 | NOT 5 NOT 6 | Input Channel Control bits (Appendix 2) |
| 0 | 0 | NOT 5 NOT 6 | Input chip control bits (Appendix 3) |
| 0 | X | 5 | Input system control bits (Appendix 4) |
| | | | INPUT D/A VALUES |
| 1 | 0 | NOT 5 NOT 6 | Input calibration attenuator values |
| 1 | NOT 0 NOT 6 | NOT 5 NOT 6 | Input offset D/A values |
| | | | MODIFY NEXT SERIAL OUTPUT |
| 0 | 6 | NOT 6 | Output channel control bits |
| 1 | 6 | NOT 6 | Output offset D/A values |
| X | X | 6 | Output system control bits, chip control bits, calibration D/A values and contents of status register |

APPENDIX 2
CHANNEL CONTROL BITS 1 bit for channel power control
 0 = channel power on (default)
 1 = channel power off
1 bit to determine right leg drive signal route

APPENDIX 2
CHANNEL CONTROL BITS

0 = RLD buffer output tied to RLD-IN signal (default)
1 = RLD buffer output external only
3 bits for front end channel configuration
000 = pad open, insto R off, A/D input at ground
001 = pad open, insto R off, A/D input at calibration
010 = pad is A/D, insto R off, A/D input is signal
011 = pad is RLD, insto R off, A/D input at ground
100 = pad is insto R, A/D input at ground
101 = pad is insto R, A/D input at calibration
110 = pad is insto R, A/D input is signal
111 = same as 110
1 bit for offset D/A control
0 = internal/external control (default)
1 = external control only
1 bit for parity, 8 bits not used

APPENDIX 3
CHIP CONTROL BITS 2 bits for preamp gain
00 = preamp gain = 2
01 = preamp gain = 4
10 = preamp gain = 16
11 = preamp gain = 32
1 bit for calibration D/A attenuation
0 = attenuation is 2/(preamp gain)
1 = attenuation is 1/16
2 bits for A/D converter mode
0 = square wave OFF (sigma-delta) (default value)
1 = square wave ON (closed loop pulse width mod.)
3 bits for offset D/A delay (continuous cycles)
000 = 1 conversion cycle (sample)
001 = 2 consecutive conversion cycles
010 = 4 consecutive conversion cycles
011 = 8 consecutive conversion cycles
100 = 16 consecutive conversion cycles
101 = 32 consecutive conversion cycles
110 = 64 consecutive conversion cycles
111 = 128 consecutive conversion cycles
2 bits for offset D/A threshold
00 = +/− 87.5% (default value)
01 = +/− 75.0%
10 = +/− 62.5%
11 = +/− 50.0%
1 bit for leads-off current source control
0 = leads-off current is ON (default value)
1 = leads-off current is OFF
3 bits for respiration channel control
000 = Channel 5 is normal ECG data (default)
001 = Production test configuration
010 = Respiration OFF, A/D input grounded
011 = Respiration OFF, A/D direct input mode
100 = Respiration ON, Calibration ON, 32 KHz
101 = Respiration ON, Calibration ON, 64 KHz
110 = Respiration ON, Calibration OFF, 32 KHz
111 = Respiration ON, Calibration OFF, 64 KHz
1 bit parity, 2 bits not used

APPENDIX 4
SYSTEM CONTROL BITS 5 bits for number of 16-bit output words
00000 = 2 (default)
00001 = same as 00000
00010 = same as 00000
00011 = 3
.
.
11110 = 30
3 bits for data clock frequency
(assuming system clock = 4.096 MHz)
000 = 32 KHz (default)
001 = 64 KHz
010 = 128 KHz
011 = 256 KHz
100 = 512 KHz
101 = 1.024 MHz
110 = 2.048 MHz
111 = 4.096 MHz
3 bits for A/D conversion rate (and resolution)
000 = 250 conversions/sec (14-bits) (default)
001 = 500 conversions/sec (13-bits)
010 = 1,000 conversions/sec (12-bits)
011 = 2,000 conversions/sec (11-bits)
100 = 4,000 conversions/sec (10-bits)
101 = 8,000 conversions/sec (9-bits)
110 = same as 101
111 = same as 101
1 bit for chopper clock ON/OFF
2 bits for chopper state when OFF
0 = chopper clock is ON
1 = use state control bits
00 = CHOP1 = low, CHOP2 = high
01 = CHOP1 = low, CHOP2 = high
10 = CHOP1 = high, CHOP2 = low
11 = CHOP1 = high, CHOP2 = high
1 parity bit, 3 bits not used

What is claimed is:

1. An electronic differential amplifier circuit comprising;
first stage amplifier means for receiving an input voltage and a gain feedback voltage and for generating a pair of first stage outputs by differentially amplifying said input voltage and said gain feedback voltage;
wherein said first stage amplifier means is chopper stabilized; and
second stage amplifier means for receiving said pair of first stage outputs and for generating a pair of second stage outputs by differentially amplifying said pair of first stage outputs;
wherein said pair of second stage outputs further comprise a negative gain second stage output and a positive gain second stage output; and
second stage common mode feedback means for receiving said pair of second stage outputs and for generating an average voltage by summing said pair of second stage outputs and for generating a second stage common mode feedback voltage by differentially amplifying said average voltage and a ground voltage;
wherein said second stage common mode feedback means is chopper stabilized; and
gain feedback means for receiving said negative gain second stage output and for generating said gain feedback voltage by forming a fraction of said negative gain second stage output.

2. An electronic differential amplifier circuit as in claim 1 wherein said first stage amplifier further comprises;
a first PMOS amplifier transistor having a gate connected to said input voltage, a source connected to a common bias current source, and a drain connected to a source of a first PMOS cascode transistor; said first PMOS cascode transistor having a drain connected to a source of a second PMOS cascode transistor; said second PMOS cascode transistor having a drain connected to a first output in said pair of first stage outputs and to a drain of a first NMOS cascode transistor; said first NMOS cascode transistor having a source connected to a drain of a second NMOS cascode transistor; said second NMOS cascode transistor having a source connected to a supply voltage; and a second PMOS amplifier transistor having a gate connected to said gain feedback voltage, a source connected to said common bias current source, and a drain connected to a source of a third PMOS cascode transistor; said third PMOS cascode transistor having a drain connected to a source of a fourth PMOS cascode transistor; said fourth PMOS cascode transistor having a drain connected to a second output in said pair of first stage outputs and to a drain of a third NMOS cascode transistor; said third NMOS cascode transistor having a source connected to a drain of a fourth NMOS cascode transistor; said fourth NMOS cascode transistor having a source connected to said supply voltage.

3. An electronic differential amplifier circuit comprising:

first chopper means for receiving an input voltage and a gain feedback voltage and for generating a pair of first chopper outputs by chopping said input voltage and said gain feedback voltage; and first stage signal amplifier means for receiving said pair of first chopper outputs and for generating a pair of first stage outputs by differentially amplifying said pair of first chipper outputs;

wherein said first stage signal amplifier means has a first stage common bias current; and first stage common mode feedback amplifier means for receiving said pair of first stage outputs and a first reference voltage and for generating a first average by summing said pair of first stage outputs and for generating a first stage common mode bias feedback voltage by differentially amplifying said first average and said first reference voltage;

wherein said first stage common mode bias feedback voltage controls said first stage common bias current; and second chopper means for receiving said pair of first stage outputs and for generating a pair of second chopper outputs by chopping said pair of first stage outputs;

wherein said second chopper means is synchronous with said first chopper means; and second stage signal amplifier means for receiving said pair of second chopper outputs and for generating a pair of second stage outputs by differentially amplifying said pair of second chopper outputs;

wherein said pair of second stage outputs further comprise a negative gain second stage output and a positive gain second stage output; and wherein said second stage signal amplifier means has a pair of variable output loads; and third chopper means for receiving said second stage outputs and a ground voltage and for generating a second average by summing said pair of second stage outputs and for generating a pair of third chopper outputs by chopping said second average and said ground voltage; and second stage common mode feedback amplifier means receiving said pair of third chopper outputs and for generating a pair of second stage common mode feedback voltages by differentially amplifying said pair of third chopper outputs; and fourth chopper means for receiving said pair of second stage common mode feedback voltages and for generating a pair of fourth chopper outputs by chopping said pair of second stage common mode feedback voltages; and current mirror means for receiving said pair of fourth chopper outputs and for converting said pair of fourth chopper outputs to a second stage load control voltage;

wherein said second stage load control voltage controls said pair of variable output loads; and gain feedback means for receiving said negative gain second stage output and for generating said gain feedback voltage by forming a fraction of said negative gain second stage output.

4. An electronic differential amplifier circuit as in claim 3 wherein said first stage amplifier means further comprises;

a first PMOS amplifier transistor having a gate connected to a first output of said pair of first chopper outputs, a source connected to said first stage common bias current, and a drain connected to a source of a first PMOS cascode transistor; said first PMOS cascode transistor having a drain connected to a source of a second PMOS cascode transistor; said second PMOS cascode transistor having a drain connected to a first output in said pair of first stage outputs and to a drain of a first NMOS cascode transistor; said first NMOS cascode transistor having a source connected to a drain of a second NMOS cascode transistor; said second NMOS cascode transistor having a source connected to a supply voltage; and a second PMOS amplifier transistor having a gate connected to a second output of said pair of first chopper outputs, a source connected to said first stage common bias current, and a drain connected to a source of a third PMOS cascode transistor; said third PMOS cascode transistor having a drain connected to a source of a fourth PMOS cascode transistor; said fourth PMOS cascode transistor having a drain connected to a second output in said pair of first stage outputs and to a drain of a third NMOS cascode transistor; said third NMOS cascode transistor having a source connected to a drain of a fourth NMOS cascode transistor; said fourth NMOS cascode transistor having a source connected to said supply voltage.

5. An electronic differential amplifier circuit as in claim 4 wherein said first stage common mode feedback amplifier means further comprises means for receiving said pair of first stage outputs and a first reference voltage and for generating a first average by summing said pair of first stage outputs and for generating a first stage common mode load feedback voltage by differentially amplifying said first average and said first reference voltage;

wherein said first stage common mode load feedback voltage is connected to a gate of said second NMOS cascode transistor and a gate of said fourth NMOS cascode transistor.

6. An electronic differential amplifier circuit comprising:

first and second input voltages; and first and second input transistors, each having a source connected to a first supply voltage and a gate connected to said first input voltage; and third and fourth input transistors, each having a source connected to said first supply voltage and a gate connected to said second input voltage; and a first output voltage connected to a drain of said second input transistor and to a drain of a first variable load transistor and to a drain of a first common feedback transistor; and a second output voltage connected to a drain of said fourth input transistor and to a drain of a second variable load transistor and to a drain of a second common feedback transistor; and wherein a drain of said first input transistor is connected to a first input current source load and to a gate of said second variable load transistor; and wherein a drain of said second input transistor is connected to a second input current source load and to a gate of said first variable load transistor; and wherein a source of said first and second variable load transistors and said first and second common feedback transistors is connected to a second supply voltage; and averaging means for receiving said first and second output voltages and for generating an average output voltage by summing said first and second output voltages; and first chopper means for receiving said average voltage and a ground voltage and for generating first and second chopper outputs by chopping said average output voltage and said ground voltage; and first feedback amplifier transistor having a source connected to a feedback amplifier common bias current source and a gate connected to said first chopper output; and second feedback amplifier transistor having a source connected to said feedback amplifier common bias current source and a gate connected to said second chopper output; and a first feedback output connected to a drain of said first feedback amplifier transistor and to a first feedback current source load and to a drain of a first feedback variable current source load and to a gate of a second feedback variable load; and a second feedback output connected to a drain of said second feedback amplifier transistor and to a second feedback current source load and to a drain of said second feedback variable current source load and to a gate of said first feedback variable load; and wherein a source of said first and second feedback variable current source loads is connected to said first supply voltage; and second chopper means for receiving said first and second feedback outputs and for generating a pair of second chopper outputs by amplifying and chopping said first and second feedback outputs; and current mirror means for receiving said pair of second chopper outputs and for generating a common feedback voltage from said pair of second chopper outputs;

wherein said common feedback voltage is connected to a gate of said first and second common feedback transistors.

* * * * *